(12) United States Patent
Hillisch et al.

(10) Patent No.: US 6,958,327 B1
(45) Date of Patent: Oct. 25, 2005

(54) 18 NORSTEROIDS AS SELECTIVELY ACTIVE ESTROGENS

(75) Inventors: Alexander Hillisch, Jena (DE); Werner Boidol, Berlin (DE); Wolfgang Schwede, Berlin (DE); Peter Esperling, Berlin (DE); Gerhard Sauer, Berlin (DE); Christa Hegele-Hartung, Muelheim/Ruhr (DE); Uwe Kollenkirchen, Berlin (DE); Karl-Heinrich Fritzemeier, Berlin (DE)

(73) Assignee: Schering, AG, Berlin (DE)

( * ) Notice: Subject to any disclaimer, the term of this patent is extended or adjusted under 35 U.S.C. 154(b) by 0 days.

(21) Appl. No.: 10/111,933

(22) PCT Filed: Nov. 2, 2000

(86) PCT No.: PCT/EP00/10804

§ 371 (c)(1),
(2), (4) Date: Oct. 8, 2002

(87) PCT Pub. No.: WO01/32680

PCT Pub. Date: May 10, 2001

Related U.S. Application Data

(60) Provisional application No. 60/188,197, filed on Mar. 10, 2000.

(30) Foreign Application Priority Data

Nov. 2, 1999 (DE) .......................................... 199 54 105

(51) Int. Cl.$^7$ .............................. A61K 31/56; C07J 1/00

(52) U.S. Cl. ....................... 514/182; 552/613; 552/625; 552/628; 552/629; 552/630

(58) Field of Search .......................... 514/182; 552/628, 552/613, 625, 629, 630

(56) References Cited

U.S. PATENT DOCUMENTS

| | | | |
|---|---|---|---|
| 3,016,389 A | * | 1/1962 | Johns .......................... 552/558 |
| 3,407,219 A | | 10/1968 | Chinn |
| 3,574,197 A | | 4/1971 | Prezewowsky et al. |
| 3,578,829 A | | 5/1971 | Stein et al. |
| 3,755,384 A | | 8/1973 | Browne et al. |
| 4,605,649 A | | 8/1986 | Liehr |
| 4,705,783 A | | 11/1987 | Crowe et al. |

FOREIGN PATENT DOCUMENTS

| | | |
|---|---|---|
| GB | 1298974 | 12/1972 |
| WO | WO 0063228 | 10/2000 |

OTHER PUBLICATIONS

William Johns, "Retropinacol Rearrangement of Estradiol 3-methyl Ether." J. Organic Chemistry, 26, pp. 4583–4591, 1961.*

Ivanova, et al., "Some Chemical Transformations or methyl ether of cis–18–nor–delta–9(11)–estra–15, 17–dione" Chemical Abstracts, vol. 63, No. 5, Abstract No. 5705c, (1965).

W.F. Johns, , "Retropinacol Rearrangement of Estradiol 3-Methyl Ether"; Journal of Organic Chemistry, Bd. 26, 1961, pp. 4583–4591, p. 4584; Examples 19, 20.

R. A. Edgren, et al., "Estrogenic Effects of 18–nor–17–beta. estradiol and 18–nore–estrone", Chemical Abstracts vol. 55, No. 6, Abstract No. 5754f (1961).

W.F. Johns, "Synthesis of 18,19–Dinor Steroids"; Journal of the American Chemical Society., Bd. 80, Nr. 23, (1958), pp. 6456–6457.

Kanazawa, Gilchi; "Clinical Effect of a Contraceptive, Sophia 32", Chemical Abstracts, Acceptance No. 72:18893 (1969).

(Continued)

*Primary Examiner*—Barbara P. Badio
(74) *Attorney, Agent, or Firm*—Millen, White, Zelano & Branigan, P.C.

(57) ABSTRACT

The invention relates to novel 18-norsteroids (gonatrienes) of general formula (I), wherein $R^1$, $R^2$, $R^3$, $R^6$, $R^7$, $R^8$, $R^9$, $R^{11}$, $R^{11'}$, $R^{14}$, $R^{15}$, $R^{15'}$, $R^{16}$, $R^{17}$ and $R^{17'}$ have the meaning cited in the description, and to the use of said compounds as pharmaceutical active ingredients. Said compounds exhibit a high affinity in vitro for estrogen receptor preparations of rat prostate and in an estrogen receptor preparation of rat uterus. Said compounds exhibit in vivo preferential activity on bones as compared to the uterus and/or significant activity with regard to stimulating the expression of 5HT2a-receptors and transporter molecules. The invention also relates to the production of said compounds, therapeutic use and galenic form of said compounds contained in the novel compounds of invention. The invention also relates to utilization of steroids based on the gonatriene molecular skeleton in order to treat estrogen deficiency-induced diseases and disorders, in addition to the use of said gonatriene structural component in the total structure of compounds which dissociate to produce enhanced estrogen activity in bone as compared to the uterus (I)

35 Claims, No Drawings

OTHER PUBLICATIONS

Haihnel, Roland, et al.: "Specificity of the Estrogen Receptor of Human Uterus"; J. Steroid Biochem (1973), 4(1), 21–31.

Haihnel, Ronald, et al.: "Steroid Specificity of the Estrogen Receptor of Human Breast Carcinoma"; J. Steroid Biochem, (1974), 5(2), 119–22.

Kuhl, Alexander, et al.: 17.alpha.–(r–Chlorobenzoyl-oxy)–3–methoxy–13.alpha.–gona–1, 3, 5(10)–triene, ACTA Crystallogr., Sect. C: Cryst; Struct. Commun. (1998), C54(4), 521–523.

M. M. Coombs: "Potentially Carinogenic Cyclopenta'al-phenanthrenes(1,2–cyclopenten ophenanthranes). Part 1. A New Synthesis of 15, 16–Dihydro–17–oxo—cyclopenta'alphenanth rene and the Phenanthrene Analogue of 18–Norestrone Methyl Ether", Journal of the Chemical Society, Section C: Organic Chemistry., Nr. 10,(1966), 955–962.

Li Jonathan, J. et al., "Carcinogenic Activities of Various Steroidal and Nonsterioidal Estrogens in the Hamster Kindney: Relation to Hormonal Activity and Cell Proliferation", Cancer Research, Bd. 55, Nr. 19 (1995), pp. 4347–4351.

Dence Carmen S., et al: Carbon–11–labeled Estrogens as Potential Imaging Agents for Breast Tumors; Nuclear Medicine and Biology, Bd. 23, Nr. 4 (1996), pp. 491–496.

Lobaccaro Carole, et al: "Steroidal Affinity Labels of the Estrogen Receptor: 3. Estradiol 11–beta–n–alkyl Derivatives Bearing a Terminal Electrophilic Group: Antiestrogenic and Cytotoxic Properties"; Journal of Medicinal Chemicstry, Bd. 40, Nr. 14 (1997), pp. 2217–2227.

Napolitano, et al.: "11.beta.–Substituted Estradiol Derivatives; Potential High–Affinity Carbo–11–Labeled Probes for the Estrogen Receptor: A Structure–Affinity Relationship Study"; Journal of Medicinal Chemistry, Bd. 38, Nr. 3 (1995), pp. 429–434.

Tedesco, R., et al., "7alpha,11beta–disubstituted Estrogens: Probes for the Shape of the Ligand Binding Pocket in the Estrogen Receptor"; Bioorganic & Medicinal Chemistry Letters, Bd. 7, Nr. 22, (1997), pp. 2919–2924.

Anstead, G., M. ,et al., "The Estradiol Pharmacophore: Ligand Structure–Estrogen Receptor Binding Afinity Relationships and a Model for the Receptor Binding Site"; Steroids, Structure, Function, and Regulation, Bd. 62, Nr. 3, 1. (1997), pp. 268–303.

R. B. Gabbard, et al., "Structure Activity Relationships of Estrogens." Effects of 14–Dehydrogenation and Axial Methyl Grops at c–7, c–9 and c–11; Steroids: Structure, Function, and Regulation, Bd. 41, Nr. 6, (1983), pp. 791–805.

* cited by examiner

18 NORSTEROIDS AS SELECTIVELY ACTIVE ESTROGENS

This application claims the benefit of priority of U.S. Provisional Application Ser. No. 60/188,197, filed Mar. 10, 2000, and is a National Stage of PCT/EP00/10804, filed Nov. 2, 2000.

FIELD OF THE INVENTION

This invention relates to new compounds as pharmaceutical active ingredients, which have in vitro a higher affinity to estrogen receptor preparations from rat prostates than to estrogen receptor preparations from rat uteri and in vivo a preferential action on bone in comparison to the uterus, and/or pronounced action relative to the stimulation of the expression of 5HT2a-receptors and transporters, their production, their therapeutic use and pharmaceutical dispensing forms that contain the new compounds.

The chemical compounds are novel, steroidal, tissue-selective estrogens.

BACKGROUND OF THE INVENTION

Established estrogen therapies for treatment of hormone-deficiency-induced symptoms and the protective action of estrogens on bones, brains, vessels and other organ systems.

The efficiency of estrogens in the treatment of hormone-deficiency-induced symptoms such as hot flashes, atrophy of estrogen target organs and incontinence, as well as the successful use of estrogen therapies for prevention of bone mass loss in peri- and postmenopausal women, is well documented and generally accepted (Grady et al. 1992, Ann Intern Med 117: 1016–1037). It is also well documented that estrogen replacement therapy in postmenopausal women or in women with ovarian dysfunction that is caused in some other way reduces the risk of cardiovascular diseases compared to non-estrogen-treated women (Grady et al., loc. cit.).

In addition, more recent studies confirm a protective action of estrogens against neurodegenerative diseases, such as, e.g., Alzheimer's disease (Henderson 1997, Neurology 48 (Suppl 7): S27–S35; Birge 1997, Neurology 48 (Suppl 7): S36–S41), a protective action with respect to brain functions, such as memory and learning capacity (McEwen et al. 1997, Neurology 48 (Suppl 7): S8–S15; Sherwin 1997, Neurology 48 (Suppl 7): S21–S26), as well as against hormone-deficiency-induced mood swings (Halbreich 1997, Neurology 48 (Suppl 7): S16–S20).

In addition, estrogen replacement therapy has proven effective relative to the reduction of the incidence of colorectal carcinoma (Calle, E. F. et al., 1995, J Natl Cancer Inst 87: 517–523).

In conventional estrogen or hormone replacement therapy (=HRT), natural estrogens, such as estradiol, and conjugated estrogens that consist of equine urine are used either by themselves or in combination with a gestagen. Instead of the natural estrogens, derivatives that are obtained by esterification, such as, e.g., 17β-estradiol-valerate, can also be used.

Because of the stimulating action of the estrogens that are used on the endometrium, which results in an increase of the risk of endometrial carcinoma (Harlap, S. 1992, Am J Obstet Gynecol 166: 1986–1992), estrogen/gestagen combination preparations are preferably used in hormone replacement therapy. The gestagenic component in the estrogen/gestagen combination avoids hypertrophy of the endometrium, but the occurrence of undesirable intracyclic menstrual bleeding is also linked to the gestagen-containing combination.

Selective estrogens represent a more recent alternative to the estrogen/gestagen combination preparations. Up until now, selective estrogens have been defined as those compounds that have an estrogen-like effect on the brain, bones and vascular system, owing to their antiuterotrophic (i.e., antiestrogenic) partial action, but they do not have a proliferative effect on the endometrium.

A class of substances that partially meet the desired profile of a selective estrogen are the so-called "Selective Estrogen Receptor Modulators" (SERM) (R. F. Kauffman, H. U. Bryant 1995, DNAP 8 (9): 531–539). In this case, these are partial agonists of estrogen receptor subtype ERα'. This substance type is ineffective, however, with respect to the therapy of acute postmenopausal symptoms, such as, e.g., hot flashes. As an example of a SERM, the raloxifene that was recently introduced for the indication of osteoporosis can be mentioned.

Estrogen Receptor Beta (ERβ)

Estrogen receptor β(ERβ) was recently discovered as a second subtype of the estrogen receptor (Kuiper et al. (1996), Proc. Natl. Acad. Sci. 93: 5925–5930; Mosselman, Dijkema (1996) Febs Letters 392: 49–53; Tremblay et al. (1997), Molecular Endocrinology 11: 353–365). The expression pattern of ERβ differs from that of the ERα (Kuiper et al. (1996), Endocrinology 138: 863–870). ERβ thus predominates over ERα in the rat prostate, while ERα predominates over ERβ in the rat uterus. Areas in which in each case only one of the two ER-subtypes is expressed were identified in the brain (Shugrue et al. (1996), Steroids 61: 678–681; Li et al. (1997), Neuroendocrinology 66:63–67). ERβ is expressed in, i.a., areas that are considered to be important for cognitive processes and "mood" (Shugrue et al. 1997, J Comparative Neurology 388: 507–525).

The 5HT2a-receptors and the serotonin transporters could be molecular targets for ERβ in these brain areas (G. Fink & B. E. H. Sumner 1996 Nature 383: 306; B. E. H. Sumner et al. 1999 Molecular Brain Research, in press). The neurotransmitter serotonin (5-hydroxytryptamine) is involved in the regulation of a considerable number of processes that can be impaired in menopause. In particular, the effects of menopause on moods and cognition are related to the serotonergic system. Estrogen replacement therapy has proven to be effective with respect to the treatment of these estrogen-deficiency-induced symptoms, possibly by modulation of serotonin receptor and transporter expression.

Other organ systems with comparatively higher ERβ-expression comprise the bones (Onoe, Y. et al., 1997, Endocrinology 138: 4509–4512), the vascular system (Register, T. C.; Adams, M. R. 1998, J. Steroid Molec Biol 64: 187–191), the urogenital tract (Kuiper, G. J. M. et al. 1997, Endocrinology 138: 863–870), the gastrointestinal tract (Campbell-Thopson 1997, BBRC 240: 478–483), as well as the testis (Mosselmann, S. et al. 1996 Febs Lett 392 49–53) including the spermatides (Shugrue et al. 1998, Steroids 63: 498–504). The tissue distribution suggests that estrogens regulate organ functions via ERβ. The fact that ERβ is functional in this respect also follows by studies in ERα-(ERKO) or ERβ-(βERKO)-knockout mice: ovariectomy produces bone mass loss in ERKO-mice, which can be cancelled out by estrogen substitution (Kimbro et al. 1998, Abstract OR7-4, Endocrine Society Meeting New Orleans). Estradiol in the blood vessels of female ERKO mice also inhibits vascular media and smooth muscle cell proliferation (Iafrati, M. D. et al. 1997, Nature Medicine 3: 545–548). These protective actions of estradiol are carried out in the ERKO mouse presumably via ERβ.

Observations of βERKO mice provide an indication on a function of ERβ in the prostate and bladder: in the case of older male mice, symptoms of prostate and bladder hyperplasia occur (Krege, J. H. et al. 1998, Proc Natl Acad Sci 95: 15677–15682). In addition, female ERKO mice (Lubahn, D. B. et al. 1993, Proc Natl Acad Sci 90; 11162–11166) and male ERKO mice (Hess, R. A. et al. 1997, Nature 390: 509–512) as well as female βERKO mice (Krege, J. H., 1998) have fertility disorders. Consequently, the important function of estrogens with respect to maintaining testis and ovary functions as well as fertility is confirmed.

It was possible to achieve a selective estrogen action on specific target organs by subtype-specific ligands based on the different tissue or organ distribution of the two subtypes of the ERs. Substances with a preference for ERβ compared to ERα in the in vitro receptor binding test were described by Kuiper et al. (Kuiper et al. (1996), Endocrinology 138; 863–870). A selective action of subtype-specific ligands of the estrogen receptor on estrogen-sensitive parameters in vivo was not previously shown.

The object of this invention is therefore to prepare compounds that have in vitro a dissociation with respect to the binding to estrogen receptor preparations from rat prostates and rat uteri and that have in vivo a dissociation with respect to bones rather than the uterus action. The compounds are to have in vitro a higher affinity to estrogen receptor preparations from rat prostates than to estrogen receptor preparations from rat uteri and in vivo a higher potency with respect to protection against hormone-deficiency-induced bone mass loss in comparison to uterus-stimulating action in the uterus and/or pronounced action with respect to the stimulation of the expression of the 5HT2a-receptors and transporters.

In the broader sense, a structure-action relationship, which allows for access to compounds that have the above-formulated pharmacological profile of better estrogenic action on bones than on the uterus, is to be made available by this invention.

According to the invention, the object above is achieved by the provision of gona-1,3,5(10)-triene derivatives of general formula I'

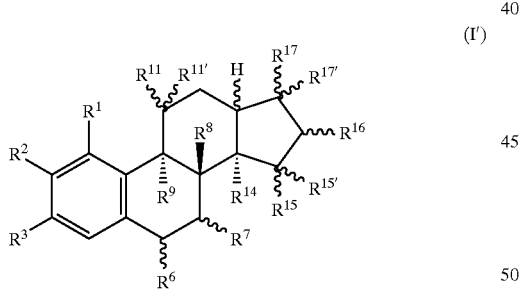

(I')

in which
R$^1$ means a halogen atom, a radical R$^{18}$— or R$^{18}$—O—, whereby R$^{18}$ means a hydrogen atom or a straight-chain or branched-chain, saturated or unsaturated hydrocarbon radical with up to 6 carbon atoms, a trifluoromethyl group, R$^2$ means a halogen atom;
a radical R$^{18}$— or R$^{18}$—O—, whereby R$^{18}$ has the meaning that is indicated under R$^1$; a group R$^{19}$SO$_2$—O—, in which R$^{19}$ is an R$^{20}$R$^{21}$N group, whereby R$^{20}$ and R$^{21}$, independently of one another, represent a hydrogen atom, a C$_1$–C$_5$ alkyl radical, a group C(O)R$^{22}$, in which R$^{22}$ can contain a straight-chain or branched-chain hydrocarbon radical with up to 12 carbon atoms, which in addition can contain up to three double bonds and/or triple bonds, a C$_3$–C$_7$ cycloalkyl radical, an aryl radical or a combination of these structural features, or, together with the N atom, a polymethylenimino radical with 4 to 6 C atoms or a morpholino radical;

R$^3$ means a group R$^{18}$—O—, R$^{19}$SO$_2$—O— or —O—C(O)R$^{22}$, with R$^{18}$, R$^{19}$ and R$^{22}$ in each case in the meaning that is indicated under R$^1$ and R$^2$, whereby in addition an aryl, heteroaryl or aralkyl radical can stand for R$^{18}$;

R$^6$ and R$^7$, independently of one another, mean a hydrogen atom, a halogen atom, a group R$^{18}$—O—, R$^{19}$SO$_2$—O— or —R$^{22}$, with R$^{18}$, R$^{19}$, and R$^{22}$ in each case in the meaning that is indicated under R$^1$ or R$^2$, a straight-chain or branched-chain, saturated or unsaturated, partially or completely halogenated alkyl group with up to 10 carbon atoms or an optionally substituted aryl, heteroaryl or aralkyl radical, R$^8$ and R$^9$, independently of one another, mean a hydrogen atom, a straight-chain or branched-chain, saturated or unsaturated, optionally partially or completely halogenated hydrocarbon radical with up to 10 carbon atoms, a group —X—R$^{18}$, in which X is an oxygen or sulfur atom, and R$^{18}$ has the meaning that is indicated under R$^1$, a halogen atom, a cyano or rhodano group, R$^{11}$ means a hydrogen atom, a halogen atom, a group R$^{18}$—O—, R$^{19}$SO$_2$—O— or —R$^{22}$, with R$^{18}$, R$^{19}$ and R$^{22}$ in each case in the meaning that is indicated under R$^1$ and R$^2$, a group —X—R$^{18}$, in which X is an oxygen or sulfur atom, and R$^{18}$ has the meaning that is indicated under R$^1$, a nitrooxy group, a straight-chain or branched-chain, saturated or unsaturated, partially or completely halogenated hydrocarbon radical with up to 10 carbon atoms or an optionally substituted aryl, heteroaryl or aralkyl radical, and R$^{11'}$ means a hydrogen atom or R$^{11}$ and R$^{11'}$ together mean a methylene group, R$^{14}$ means a hydrogen atom in α-position or a straight-chain or branched-chain alkyl, alkenyl or alkinyl group with up to 3 carbon atoms, and.

R$^{15}$ means a hydrogen atom, or

R$^{14}$ and R$^{15}$ together mean a methylene group that is optionally halogenated in one or two places;

R$^{15}$ and R$^{16}$, independently of one another, mean a hydrogen atom, a halogen atom, a group R$^{18}$—O—, R$^{19}$SO$_2$—O— or —R$^{22}$, with R$^{18}$, R$^{19}$ and R$^{22}$ in each case in the meaning that is indicated under R$^1$ or R$^2$;

R$^{17}$ and R$^{17'}$ mean a hydrogen atom and a halogen atom; a hydrogen atom and a benzyloxy group; a hydrogen atom and a group R$^{19}$SO$^2$—O—; a group R$^{18}$ and a group —C(O)R$^{22}$ or —O—C(O)R$^{22}$, with R$^{18}$, R$^{19}$ and R$^{22}$ in each case in the meaning that is indicated under R$^1$ or R$^2$; a group R$^{18}$—O— and a group R$^{18}$—; a group R$^{18}$—O— and a group —O—C(O)R$^{22}$, in all cases above with R$^{18}$, R$^{19}$, and R$^{22}$ in each case in the meaning that is indicated under R$^1$ or R$^2$; or R$^{17}$ and R$^{17'}$ together mean a group =CR$^{23}$R$^{24}$, in which R$^{23}$ and R$^{24}$, independently of one another, represent a hydrogen atom and a halogen atom, or an oxygen atom;

and one or more double bonds can be present in positions 6, 7; 7, 8; 9, 11; 11, 12; 14, 15 and 15, 16 for the treatment of estrogen-deficiency-induced diseases and conditions.

The possible substituents at carbon atoms 6, 7, 11, 15, 16, and 17 and the hydrogen atom at carbon atom 13 can be respectively in α- or β-position.

According to a variant of the invention, preferably compounds of general formula I' are used,
in which
$R^1$ means a hydrogen atom or a group $R^{18}$—O—, whereby $R^{18}$ means a hydrogen atom or a straight-chain or branched-chain, saturated or unsaturated hydrocarbon radical with up to 6 carbon atoms, $R^2$ means a hydrogen or halogen atom or a hydroxy group, $R^3$ means a group $R^{18}$—O—, $R^{19}SO_2$—O— or —O—C(O)$R^{22}$, with $R^{18}$, $R^{19}$ and $R^{22}$ in each case in the meaning that is indicated under $R^1$ or $R^2$, whereby in addition an aryl or aralkyl radical can stand for $R^{18}$;

$R^6$ means a hydrogen atom, a hydroxy group, a group $R^{22}$ in which an optionally substituted aryl, heteroaryl or aralkyl radical is in the meaning that is indicated under $R^2$, $R^7$ means a hydrogen atom, a halogen atom, a group $R^{18}$—O—, $R^{19}SO_2$—O— or —$R^{22}$, with $R^{18}$, $R^{19}$, and $R^{22}$ in each case in the meaning that is indicated under $R^1$ and $R^2$, a straight-chain or branched-chain, saturated or unsaturated, partially or completely halogenated alkyl group with up to 10 carbon atoms or an optionally substituted aryl, heteroaryl or aralkyl radical, $R^8$ and $R^9$, independently of one another, mean a hydrogen atom, a straight-chain or branched-chain, saturated or unsaturated, optionally partially or completely halogenated hydrocarbon radical with up to 10 carbon atoms, a group —X—$R^{18}$, in which X is an oxygen or sulfur atom, and $R^{18}$ has the meaning that is indicated under $R^1$, a halogen atom, a cyano or rhodano group, $R^{11}$ means a hydrogen atom, a halogen atom, a group —$R^{22}$ with $R^{22}$ in the meaning that is indicated under $R^2$, a group —X—$R^{18}$, in which X is a sulfur atom and $R^{18}$ has the meaning that is indicated under $R^1$, a straight-chain or branched-chain, saturated or unsaturated, partially or completely halogenated hydrocarbon radical with up to 10 carbon atoms or an optionally substituted aryl or heteroaryl radical, $R^{14}$ means a hydrogen atom in α-position or a straight-chain or branched-chain alkinyl group with up to 3 carbon atoms, and $R^{15}$ means a hydrogen atom or $R^{14}$ and $R^{15}$ together mean a methylene group;

$R^{15'}$ and $R^{16}$, independently of one another, mean a hydrogen atom, a halogen atom, a group $R^{18}$—O—, $R^{19}SO_2$—O— or —$R^{22}$, with $R^{18}$, $R^{19}$ and $R^{22}$ in each case in the meaning that is indicated under $R^1$ or $R^2$;

$R^{17}$ and $R^{17'}$ mean a hydrogen atom and a halogen atom; a hydrogen atom and a benzyloxy group; a hydrogen atom and a group $R^{19}SO^2$—O—; a group $R^{18}$ and a group —C(O)$R^{22}$ or —O—C(O)$R^{22}$, with $R^{18}$, $R^{19}$ and $R^{22}$ in each case in the meaning that is indicated under $R^1$ or $R^2$; a group $R^{18}$—O— and a group $R^{18}$—; a group $R^{18}$—O— and a group —O—C(O)$R^{22}$, in all cases above with $R^{18}$, $R^{19}$ and $R^{22}$ in each case in the meaning that is indicated under $R^1$ or $R^2$; and $R^{17}$ and $R^{17'}$ together mean a group =C$R^{23}R^{24}$, in which $R^{23}$ and $R^{24}$, independently of one another, represent a hydrogen atom and a halogen atom, or an oxygen atom.

Another preferred variant of this invention calls for the use of those compounds of general formula I', in which $R^1$ means a hydrogen atom, a hydroxy group or straight-chain or branched-chain $C_1$–$C_6$ alkyl group, $R^2$ means a hydrogen atom or fluorine atom or a hydroxy group, $R^3$ means a group $R^{18}$—O—, $R^{19}SO_2$—O— or —O—C(O)$R^{22}$, with $R^{18}$, $R^{19}$ and $R^{22}$ in each case in the meaning that is indicated under $R^1$ or $R^2$, whereby in addition an aryl or aralkyl radical can stand for $R^{18}$;

$R^6$ means a hydrogen atom or a hydroxy group, $R^7$ means a hydrogen atom, a fluorine or chlorine atom, a group $R^{18}$—O—, $R^{19}SO_2$—O— or —$R^{22}$, with $R^{18}$, $R^{19}$ and $R^{22}$ in each case in the meaning that is indicated under $R^1$ or $R^2$, a straight-chain or branched-chain, saturated or unsaturated, partially or completely halogenated alkyl group with up to 10 carbon atoms or an optionally substituted aryl, heteroaryl or aralkyl radical, $R^8$ and $R^9$, independently of one another, mean a hydrogen atom, a straight-chain or branched-chain, saturated or unsaturated, optionally partially or completely halogenated hydrocarbon radical with up to 10 carbon atoms, a group —X—$R^{18}$, in which X is an oxygen atom, and $R^{18}$ has the meaning that is indicated under $R^1$, a fluorine or chlorine atom or a cyano group, $R^{11}$ means a hydrogen atom, a fluorine or chlorine atom, a saturated, straight-chain or branched-chain $C_1$–$C_6$ alkyl group, a group —X—$R^{18}$, in which X is a sulfur atom and $R^{18}$ means a saturated, straight-chain or branched-chain $C_1$–$C_6$ alkyl group, a chloromethyl or chloroethyl group or an optionally-substituted aryl or heteroaryl radical, $R^{14}$ means a hydrogen atom in α-position, and $R^{15}$ means a hydrogen atom or $R^{14}$ and $R^{15}$ together mean a methylene group;

$R^{15'}$ and $R^{16}$, independently of one another, mean a hydrogen atom, a fluorine or chlorine atom or a group $R^{18}$—O or —$R^{22}$, with $R^{18}$ and $R^{22}$ in each case in the meaning that is indicated under $R^1$ or $R^2$;

$R^{17}$ and $R^{17'}$ mean a hydrogen atom and a halogen atom; a hydrogen atom and a benzyloxy group; a hydrogen atom and a group $R^{19}SO_2$—O—; a group $R^{18}$ and a group —C(O)$R^{22}$ or —O—C(O)$R^{22}$, with $R^{18}$, $R^{19}$ and $R^{22}$ in each case in the meaning that is indicated under $R^1$ or $R^2$; a group $R^{18}$—O— and a group $R^{18}$—; a group $R^{18}$—O— and a group —O—C(O)$R^{22}$, in all cases above with $R^{18}$, $R^{19}$ and $R^{22}$ in each case in the meaning that is indicated under $R^1$ or $R^2$; and $R^{17}$ and $R^{17'}$ together mean a group =C$R^{23}R^{24}$, in which $R^{23}$ and $R^{24}$, independently of one another, represent a hydrogen atom and a halogen atom, or an oxygen atom.

According to another variant, gona-1,3,5(10)-triene derivatives of general formula I' are used, in which $R^6$, $R^8$, $R^9$, $R^{14}$, $R^{15}$, $R^{15'}$ and $R^{16}$ in each case stand for a hydrogen atom, and all other substituents have the meanings that are indicated in claim 1.

If the gonatriene derivatives of general formula I' contain additional double bonds in the B-, C- and/or D-ring, then a double bond is present preferably in position 7, 8 or in position 11, 12 or two double bonds are present in positions 6, 7 and 8, 9.

Another variant of the invention are gonatriene derivatives of general formula I'
in which
$R^{17}$ and $R^{17'}$ are a group $R^{18}$—O— and a group $R^{18}$; a group $R^{18}$— and a group —O—C(O)$R^{22}$, with $R^{18}$ and $R^{22}$ in each case in the meaning that is indicated under $R^1$ or $R^2$.

Of these last-mentioned derivatives, in turn those gonatriene derivatives are preferred
in which
R$^{17}$ and R$^{17'}$ are a hydroxy group and a hydrogen atom, a C$_1$–C$_4$ alkyl group or C$_2$–C$_4$ alkenyl group
and especially preferably those
in which
R$^{17}$ and R$^{17'}$ are a hydroxy group and a hydrogen atom, a methyl, ethinyl or prop-1-inyl group.

Additional possible configurations of this invention arise from subclaims 2 to 15.

In addition to the above use of the compounds of general formula I', the invention also relates to the compounds of general formula I themselves. These are the compounds of general formula I' excluding the compounds that at carbon atoms 13, 3, 17, 9, 15 and 16 have the following substituent combinations (here, the other substituents in general formula I mean hydrogen in each case) as well as double bonds between the indicated carbon atoms (if no indication is made in the table, hydrogen is on the carbon atom in question):

| 13-H stehf | 3 | 17 (im Falle von 2 Substituenten an C17 handelt es sich beim nicht angegebenen Substituenten um ein H-Atom) | 9 | 15 | 16 | Doppelbindung zwischen | Doppelbindung zwischen |
|---|---|---|---|---|---|---|---|
| β | isopropylcarbonyloxy | =O | | | | | |
| β | OAc (Ac = Acetyl) | =O | | | | | |
| β | OAc | α-OH | | | | | |
| β | OAc | β-OH | | | | | |
| β | OAc | α-OAc | | | | | |
| β | OAc | β-OAc | | | | | |
| β | OH | =O | | | | | |
| β | OH | β-OH | | | | | |
| β | OMe (Me = Methyl) | | | | | | |
| β | OH | α-OVal | | | | | |
| β | OH | β-OVal | | | | | |
| β | OH | α-OAc | | | | | |
| β | OH | β-OAc | | | | | |
| β | OH | α-OH | | | | | |
| β | OH | β-OH | | | | | |
| β | OMe | β-OH | α-OH | | | | |
| β | OMe | β-OH | β-OH | | | | |
| β | OMe | =O | | | | | |
| β | OMe | β-Ac | | | | 8, 9 | 14, 15 |
| β | OMe | β-Ac | | α-OH | | | |
| β | OMe | β-Ac | | β-OH | | | |
| β | OMe | =O | OMe/H | | | 9, 11 | 15, 16 |
| β | OMe | β-Ac | | | | | |
| β | OMe | α-Ac | | α-OH | | | |
| β | OMe | α-Ac | | β-OH | | | |
| β | OMe | β-Ac | | | α-OH | | |
| β | OMe | β-Ac | | | β-OH | | |
| β | OMe | β-OH | | α-OMe | | | |
| β | OMe | β-OH | | β-OMe | | | |
| β | OMe | α-OH | | | | | |
| β | OMe | α-OH | | | | | |
| β | O-n-Bu (Bu = Butyl) | =O | | | | | |
| β | O-n-Bu | α-OH | | | | | |
| β | O-n-Bu | β-OH | | | | | |
| β | O-n-Bu | Ac | | | | 16, 17 | |
| β | Val (Val = Valerat) | α-Val | | | | | |
| β | Val | β-Val | | | | | |
| β | Val | α-OH | | | | | |
| β | Val | β-OH | | | | | |
| β | Val | β-OH | | | | | |
| α | OAc | =O | | | | | |
| α | OH | =O | | | | | |
| α | OMe | =O | | | | | |
| α | OMe | α-OH | | | | | |
| α | OMe | p-Cl-Benzoat | | | | | |
| α | OMe | =O | | | | 9, 11 | |
| α | OMe | β-OH | | | | | |
| α | OMe | β-OAc | | | | | |

-continued

| 13-H stehf | 3 | 17 (im Falle von 2 Substituenten an C17 handelt es sich beim nicht angegebenen Substtituenten um ein H-Atom) | 9 | 15 | 16 | Doppel- bindung zwischen | Doppel- bindung zwischen |
|---|---|---|---|---|---|---|---|
| α | OMe | α-OAc | | | | | |
| α | OMe | α-OH/ β-Me | | | α-OH | | |
| α | OMe | =O | | OMe/H | | 9, 11 | 15, 16 |
| α | O-n-Bu | =O | | | | | |
| α | O-n-Bu | α-OH | | | | | |
| α | O-n-Bu | β-OH | | | | | |

[Key to First Table Page:]
13-H steht=13-H is
(im Falle von 2 Substituenten an C17 handelt es sich beim nicht angegebenen Substituenten um ein H-atom)=(In the case of 2 substituents at C17, if unindicated substituents are an H atom)
Doppelbindung zwischen=double bond between
[Key to Second Table Page:] Valerat=valerate
Benzoat=benzoate This group of compounds named in the Table is already known; a selective estrogenic action and the use of the known compounds in the context of this invention has not yet been described, however.

The already known gonatrienes are in most cases described as intermediates, as estrogens in the conventional sense or for use in analytical processes.

In the compounds of general formulas I and I' as well as in partial structures II and II' that are described below, a fluorine, chlorine, bromine or iodine atom can always stand for a halogen atom; a fluorine atom is preferred in each case. In particular also a chlorine atom can be named as substituent for the 11β-position.

In particular, the hydrocarbon radicals, which can be partially or completely halogenated, are fluorinated radicals.

The alkoxy groups in the compounds of general formulas I and I' as well as in partial structures II and II' that are described below can contain 1 to 6 carbon atoms in each case, whereby methoxy, ethoxy, propoxy, isopropoxy and t-butyloxy groups are preferred.

As representatives of the alkylthio groups, for example, methylthio, ethylthio and trifluoromethylthio groups can be mentioned.

Within the context of this invention, an aryl radical is a phenyl radical or a 1- or 2-naphthyl radical; the phenyl radical is preferred.

Unless expressly indicated, aryl always also includes a heteroaryl radical. Examples of a heteroaryl radical are the 2-, 3- or 4-pyridinyl, the 2- or 3-furyl, the 2- or 3-thienyl, the 2- or 3-pyrrolyl, the 2-, 4- or 5-imidazolyl, the pyrazinyl, the 2-, 4- or 5-pyrimidinyl or 3- or 4-pyridazinyl radical.

As substituents for an aryl or heteroaryl radical, for example, a methyl-, ethyl-, trifluoromethyl-, pentafluoroethyl-, trifluoromethylthio-, methoxy-, ethoxy-, nitro-, cyano-, halogen-(fluorine, chlorine, bromine, iodine), hydroxy-, amino-, mono($C_{1-8}$ alkyl) or di($C_{1-8}$ alkyl)amino can be mentioned, whereby both alkyl groups are identical or different, di(aralkyl)amino, whereby both aralkyl groups are identical or different.

As representatives of straight-chain or branched-chain hydrocarbon radicals with 1 to at most 12 carbon atoms, for example, methyl, ethyl, propyl, isopropyl, butyl, isobutyl, tert-butyl, pentyl, isopentyl, neopentyl, heptyl, hexyl, decyl, undecyl and dodecyl can be mentioned; methyl, ethyl, propyl and isopropyl are preferred.

As a $C_3$–$C_7$ cycloalkyl group, a cyclopropyl, butyl, pentyl, hexyl or heptyl group can be cited.

An aralkyl radical is a radical that contains up to 14, preferably 6 to 10, C atoms in the ring, and 1 to 8, preferably 1 to 4, C atoms in the alkyl chain. Thus, as aralkyl radicals, for example, benzyl, phenylethyl, naphthylmethyl, naphthylethyl, furylmethyl, thienylethyl, and pyridypropyl can be considered. The rings can be substituted in one or more places by halogen, OH, O-alkyl, $CO_2H$, $CO_2$-alkyl, —$NO_2$, —$N_3$, —CN, $C_1$–$C_{20}$ alkyl, $C_1$–$C_{20}$ acyl, or $C_1$–$C_{20}$ acyloxy groups.

The alkyl groups can be partially or completely fluorinated or substituted by 1–5 halogen atoms, hydroxy groups or $C_1$–$C_4$ alkoxy groups.

With a $C_2$–$C_3$ alkenyl radical or $C_2$–$C_3$ alkinyl radical, a vinyl or allyl radical or an ethinyl, 1- or 2-propinyl radical is meant.

As perfluorinated alkyl groups, for example, trifluoromethyl, pentafluoroethyl and nonafluorobutyl can be mentioned. Representatives of partially fluorinated alkyl groups are, for example, 2,2,2-trifluoroethyl, 5,5,5,4,4-pentafluoropentyl, 6,6,6,5,5,4,4,3,3-nonafluorohexyl, etc.

Monochloromethylene, monofluoromethylene or difluoromethylene can stand for the halogen-substituted 14,15-methylene group.

Other variants of the invention provide one or more optionally conjugated double bonds in rings B, C and D of the estratriene skeleton, specifically one or more double bonds in positions 6, 7; 7, 8; 9, 11; 11, 12; 14, 15 and 15, 16. In this case, a double bond is preferably in position 7, 8 or in position 11, 12, or two double bonds are in positions 6, 7 and 8, 9 (i.e., the naphthalene system is formed together with the aromatic A-ring).

One or both hydroxyl groups at C atoms 3 and 17 can be esterified with an aliphatic, straight-chain or branched-chain, saturated or unsaturated $C_1$–$C_{14}$ mono- or polycarboxylic acid or an aromatic carboxylic acid or with an α- or β-amino acid.

Suitable as such carboxylic acids for esterification are, for example:

Monocarboxylic acids: formic acid, acetic acid, propionic acid, butyric acid, isobutyric acid, valeric acid, isovaleric acid, pivalic acid, lauric acid, myristic acid, acrylic acid, propiolic acid, methacrylic acid, crotonic acid, isocrotonic acid, oleic acid, elaidic acid.

Esterification with acetic acid, valeric acid or pivalic acid is preferred.

Dicarboxylic acids: oxalic acid, malonic acid, succinic acid, glutaric acid, adipic acid, pimelic acid, suberic acid, azelaic acid, sebacic acid, maleic acid, fumaric acid, muconic acid, citraconic acid, and mesaconic acid.

Aromatic carboxylic acids: benzoic acid, phthalic acid, isophthalic acid, terephthalic acid, naphthoic acid, o-, m- and p-toluic acid, hydratropic acid, atropic acid, cinnamic acid, nicotinic acid, and isonicotinic acid.

Esterification with benzoic acid is preferred.

As amino acids, the representatives of these classes of substances that are known sufficiently to one skilled in the art are suitable, for example, alanine, β-alanine, arginine, cysteine, cystine, glycine, histidine, leucine, isoleucine, phenylalanine, proline, etc.

Esterification with β-alanine is preferred.

According to this invention, the compounds below are preferred:

11β-Fluoro-gona-1,3,5(10)-triene-3,17-diol
11β-chloro-gona-1,3,5(10)-triene-3,17-diol
11β-methyl-gona-1,3,5(10)-triene-3,17-diol
11β-ethyl-gona-1,3,5(10)-triene-3,17-diol
11β-phenyl-gona-1,3,5(10)-triene-3,17-diol
7α-fluoro-gona-1,3,5(10)-triene-3,17-diol
7α-methyl-gona-1,3,5(10)-triene-3,17β-diol
7α-phenyl-gona-1,3,5(10)-triene-3,17β-diol
7α-methyl-gona-1,3,5(10)-triene-3,17-diol
7β-fluoro-gona-1,3,5(10)-triene-3,17-diol
7β-methyl-gona-1,3,5(10)-triene-3,17β-diol
7β-phenyl-gona-1,3,5(10)-triene-3,17β-diol
7β-methyl-gona-1,3,5(10)-triene-3,17-diol
7β-ethyl-gona-1,3,5(10)-triene-3,17β-diol
7β-ethyl-gona-1,3,5(10)-triene-3,17α-diol
7β-ethyl-13α-H-gona-1,3,5(10)-triene-3,17α-diol
2-fluoro-gona-1,3,5(10)-triene-3,17β-diol
17α-(1-propinyl)-gona-1,3,5(10)-triene-3,17β-diol
11-methylene-17α-(1-propinyl)-gona-1,3,5(10)-triene-3,17β-diol
11β-methyl-17α-(1-propinyl)-gona-1,3,5(10)-triene-3,17β-diol
11β,17α-dimethyl-gona-1,3,5(10)-triene-3,17β-diol
11β,17β-dimethyl-gona-1,3,5(10)-triene-3,17α-diol
13α-H-18-nor-estradiol
18-nor-estriol
11β-fluoro-gona-1,3,5(10)-triene-1,3,17-triol
11β-chloro-gona-1,3,5(10)-triene-1,3,17-triol
11β-methyl-gona-1,3,5(10)-triene-1,3,17-triol
11β-ethyl-gona-1,3,5(10)-triene-1,3,17-triol
11β-phenyl-gona-1,3,5(10)-triene-1,3,17-triol
7α-fluoro-gona-1,3,5(10)-triene-1,3,17-triol
7α-methyl-gona-1,3,5(10)-triene-1,3,17-triol
7α-phenyl-gona-1,3,5(10)-triene-1,3,17-triol
7α-methyl-gona-1,3,5(10)-triene-1,3,17-triol
7β-fluoro-gona-1,3,5(10)-triene-1,3,17-triol
7β-methyl-gona-1,3,5(10)-triene-1,3,17-triol
7β-phenyl-gona-1,3,5(10)-triene-1,3,17-triol
7β-methyl-gona-1,3,5(10)-triene-1,3,17-triol
2-fluoro-gona-1,3,5(10)-triene-1,3,17-triol
17α-(1-propinyl)-gona-1,3,5(10)-triene-1,3,17-triol
11-methylene-17α-(1-propinyl)-gona-1,3,5(10)-triene-1,3,17-triol
11β-methyl-17α-(1-propinyl)-gona-1,3,5(10)-triene-1,3,17-triol
11β,17α-dimethyl-gona-1,3,5(10)-triene-1,3,17-triol
11β,17β-dimethyl-gona-1,3,5(10)-triene-1,3,17-triol Within the context of the aspect of use of the invention, the use of the already known compound 18-nor-17β-estradiol is preferred in addition to the new compounds that are listed above.

Another aspect of this invention relates to the use of the structural part of formula II (gona-1,3,5(10)-structural part)

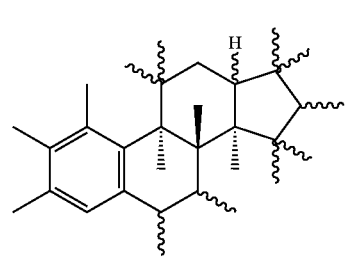

(II)

as a component of the total structure of compounds that have a dissociation in favor of their estrogenic action on bone in comparison to the uterus.

In addition to the aromatic A-ring, one or more optionally conjugated double bonds can be present in the B-, C- and/or D-ring in positions 6, 7; 7, 8; 9, 11; 11, 12; 14, 15 and 15, 16.

The possible substituents in carbon atoms 6, 7, 11, 15, 16, and 17, and the hydrogen atom in carbon atom 13 can be respectively in α- or β-position.

This invention preferably relates to those structural parts of general formula II′

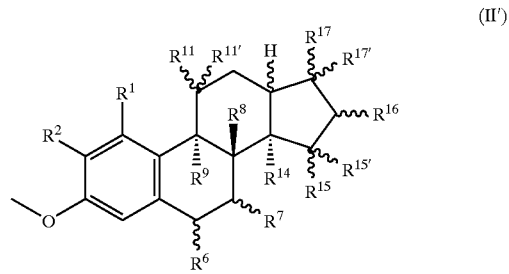

(II′)

in which radicals $R^1$ to $R^{17}$ have the meanings that are indicated in general formula I.

In addition to the aromatic A-ring, these structural parts can also have one or more, optionally conjugated, double bonds in the B-, C- and/or D-ring.

The possible substituents at carbon atoms 6, 7, 11, 15, 16, and 17 can in turn be in each case in the α- or β-position, and the hydrogen atom at carbon atom 13 can preferably be in β-position.

The esters of the 18-nor-steroids according to the invention have advantages as prodrugs compared to the unesterified active ingredients with respect to their method of administration, their type of action, strength and duration of action.

The 18-nor-steroid sulfamates according to the invention also have pharmacokinetic and pharmacodynamic advantages. In this respect, effects were already described in the case of sulfamates that are derived from estrogens with a 13-methyl group (J. Steroid Biochem. Molec. Biol, 55, 395–403 (1995); Exp. Opinion Invest. Drugs 7, 575–589 (1998)).

In this patent application, steroids on which the gonatriene-(=18-nor-estratriene) skeleton is based for treatment of estrogen-receptor β-mediated diseases and conditions are described as selective estrogens, which have in vitro dissociation with respect to binding to estrogen receptor preparations of rat prostates and rat uteri and which have in vivo dissociation with respect to bone action in comparison to uterus action: the substances act in a bone-protective manner over a wide dose range without stimulating the uterus. In the same dose range, their liver action is small.

In addition, the substances exert estrogen-like action on the vascular system and brain functions. Substances with higher binding to the rat prostates—compared to the rat-uterus-estrogen receptor—are more powerful with respect to the increase of the expression of the serotonin receptors and transporters, in comparison to their positive effect on the LH-release. Processes in which regulation of the neurotransmitter serotonin is involved are therefore influenced advantageously, and the compounds according to the invention then exert an advantageous influence especially on mood and cognition.

They can be used in humans as estrogens in the context described in WO 97/45125 for the production of medications for influencing the level of serotonin or serotonin mRNA.

It has been found that the nor-steroids according to the invention are suitable as selective estrogens for the treatment of various conditions and diseases, which are characterized by a higher content of estrogen receptor β than estrogen receptor α in the corresponding target tissue or organ.

The invention also relates to pharmaceutical preparations that contain at least one compound of general formula I (or physiologically compatible addition salts with organic and inorganic acids of them) and the use of the compounds of general formula I' for the production of pharmaceutical agents, especially for the indications below.

The compounds can be used for the following indications both after oral and parenteral administration.

The novel selective estrogens that are described in this patent can be used as individual components in pharmaceutical preparations or in combination especially with antiestrogens or gestagens. Especially preferred is the combination of selective estrogens with ERα-selective antiestrogens, or with antiestrogens that are peripherally-selectively active, i.e., that do not pass through the blood-brain barriers.

The substances and the pharmaceutical agents that contain them are especially suitable for the treatment of peri- and postmenopausal symptoms, especially hot flashes, sleep disturbances, irritability, mood swings, incontinence, vaginal atrophy, and hormone-deficiency-induced emotional diseases. The substances for hormone substitution and therapy of hormone-deficiency-induced symptoms in the case of surgical, medicinal or ovarian dysfunction that is caused in some other way are also suitable. Prevention of bone mass loss in postmenopausal women, in women who have undergone hysterectomies or in women who were treated with LHRH agonists or LHRH antagonists is also part of this.

The compounds are also suitable for alleviating symptoms of male menopause and female menopause, i.e., for male and female hormone replacement therapy (HRT), specifically both for prevention and for treatment, in addition for treatment of symptoms that are accompanied by a dysmenorrhea as well as for treatment of acne.

In addition, the substances can be used for prophylaxis against hormone-deficiency-induced bone mass loss and osteoporosis, for prevention of cardiovascular diseases, especially vascular diseases such as arteriosclerosis, for inhibition of the proliferation of arterial smooth muscle cells, for treatment of primary pulmonary high blood pressure and for prevention of hormone-deficiency-induced neurodegenerative diseases, such as Alzheimer's disease, as well as hormone-deficiency-induced impairment of memory and learning capacity.

In addition, the substances can be used for treatment of inflammatory diseases and diseases of the immune system, especially auto-immune diseases, such as, e.g., rheumatoid arthritis.

In addition, the compounds can be used for the treatment of male fertility disorders and prostatic diseases.

The compounds can also be used in combination with the natural vitamin D3 or with calcitriol analogues for bone formation or as supporting therapies to therapies that cause bone mass loss (for example, therapy with glucocorticoids, chemotherapy).

Finally, the compounds of general formula I' can be used in connection with progesterone receptor antagonists, specifically especially for use in hormone replacement therapy and for treatment of gynecological disorders.

A therapeutic product that contains an estrogen and a pure antiestrogen for simultaneous, sequential or separate use for the selective estrogen therapy of perimenopausal or postmenopausal conditions is already described in EP-A 0 346 014.

The amount of a compound of general formula I' that is to be administered varies within a wide range and can cover any effective amount. On the basis of the condition that is to be treated and the type of administration, the amount of the compound that is administered can be 0.01 μg/kg–10 mg/kg of body weight, preferably 0.04 Ag/kg–1 mg/kg of body weight, per day.

In humans, this corresponds to a dose of 0.8 μg to 800 mg, preferably 3.2 μg to 80 mg, daily.

According to the invention, a dosage unit contains 1.6 μg to 200 mg of one or more compounds of general formula I.

The compounds according to the invention and the acid addition salts are suitable for the production of pharmaceutical compositions and preparations. The pharmaceutical compositions or pharmaceutical agents contain as active ingredient one or more of the compounds according to the invention or their acid addition salts, optionally mixed with other pharmacologically or pharmaceutically active substances. The production of the pharmaceutical agents is carried out in a known way, whereby the known and commonly used pharmaceutical adjuvants as well as other commonly used vehicles and diluents can be used.

As such vehicles and adjuvants, for example, those are suitable that are recommended or indicated in the following bibliographic references as adjuvants for pharmaceutics, cosmetics and related fields: Ullmans Encyklopädie der technischen Chemie [Ullman's Encyclopedia of Technical Chemistry], Volume 4 (1953), pages 1 to 39; Journal of Pharmaceutical Sciences, Volume 52 (1963), page 918 ff., issued by Czetsch-Lindenwald, Hilfsstoffe für Pharmazie und angrenzende Gebiete [Adjuvants for Pharmaceutics and Related Fields]; Pharm. Ind., Issue 2, 1961, p. 72 and ff.: Dr. H. P. Fiedler, Lexikon der Hilfsstoffe für Pharmazie, Kosmetik und angrenzende Gebiete [Dictionary of Adjuvants for Pharmaceutics, Cosmetics and Related Fields], Cantor KG, Aulendorf in Württemberg 1971.

The compounds can be administered orally or parenterally, for example intraperitoneally, intramuscularly, subcutaneously or percutaneously. The compounds can also be implanted in the tissue.

For oral administration, capsules, pills, tablets, coated tablets, etc., are suitable. In addition to the active ingredient, the dosage units can contain a pharmaceutically compatible vehicle, such as, for example, starch, sugar, sorbitol, gelatin, lubricant, silicic acid, talc, etc.

For parenteral administration, the active ingredients can be dissolved or suspended in a physiologically compatible diluent. As diluents, very often oils with or without the addition of a solubilizer, a surfactant, a suspending agent or an emulsifying agent are used. Examples of oils that are used are olive oil, peanut oil, cottonseed oil, soybean oil, castor oil and sesame oil.

The compounds can also be used in the form of a depot injection or an implant preparation, which can be formulated so that a delayed release of active ingredient is made possible.

As inert materials, implants can contain, for example, biodegradable polymers, or synthetic silicones such as, for example, silicone rubber. In addition, for percutaneous administration, the active ingredients can be added to, for example, a patch.

For the production of intravaginal systems (e.g., vaginal rings) or intrauterine systems (e.g., pessaries, coils, IUDs, mirena®) that are loaded with active compounds of general formula I' for local administration, various polymers are suitable, such as, for example, silicone polymers, ethylene vinyl acetate, polyethylene or polypropylene.

To achieve better bio-availability of the active ingredient, the compounds can also be formulated as cyclodextrin clathrates. For this purpose, the compounds are reacted with α-, β-, or γ-cyclodextrin or derivatives of the latter (PCT/EP95/02656).

According to the invention, the compounds of general formula I' can also be encapsulated with liposomes.

Methods

Estrogen Receptor Binding Studies

The binding affinity of the new selective estrogens was tested in competitive experiments with use of 3H-estradiol as a ligand to estrogen receptor preparations of rat prostates and rat uteri. The preparation of prostate cytosol and the estrogen receptor test with prostate cytosol was carried out as described by Testas et al. (1981) (Testas, J. et al., 1981, Endocrinology 109; 1287–1289).

The preparation of rat uterus cytosol, as well as the receptor test with the ER-containing cytosol were basically performed as described by Stack and Gorski, 1985 (Stack, Gorski 1985, Endocrinology 117, 2024–2032) with some modifications as described in Fuhrmann et al. (1995) (Fuhrmann, U. et al. 1995, Contraception 51: 45–52).

The substances that are described in this patent have higher binding affinity to the estrogen receptor of rat prostates than to estrogen receptors of rat uteri. In this case, it is assumed that ERβ predominates in the rat prostates over ERα, and ERα predominates in rat uteri over ERβ. Table 1 shows that the ratio of the binding to prostate and uterus receptors qualitatively coincides with the quotient of relative binding affinity (RBA) to human ERβ and ERα of rats (according to Kuiper et al. (1996), Endocrinology 138: 863–870) (Table 1).

Table 2 shows the results of the compound to be used according to the invention 18-nor-17β-estradiol (compound A) as well as for the compounds according to the invention 11β,17α-dimethyl-gona-1,3,5(10)-triene-3,17β-diol. (compound B), 11-methylene-17α-(1-propinyl)-gona-1,3,5(10)-triene-3,17β-diol (compound C), 17α-(1-propinyl)-gona-1,3,5(10)-triene-3,17β-diol (compound D) as well as 11β-methyl-17α-(1-propinyl)-gona-1,3,5(10)-triene-3,17β-diol (compound E).

The compounds A, B, C, D and E show a higher binding affinity to the estrogen receptor from the rat prostate than to the estrogen receptor from the rat uterus.

In addition, the predictability of the 'prostate-ER versus the uterus-ER test system' was confirmed with respect to tissue-selective action by in vivo studies. Substances with a preference for prostate-ER are dissociated in vivo with respect to bone and uterus action in favor of action on bones.

Bone Studies

Three-month-old female rats are ovariectomized and treated once daily with the test compound immediately after the operation for 28 days. The administration is carried out subcutaneously in arachis oil/ethanol. The animals are sacrificed on the day after the last administration, and tibia as well as uteri are removed. The uteri are weighed, fixed and worked up for histological studies. The determination of bone density is carried out ex vivo on prepared long bones by means of pQCT (quantitative computer tomography). The measurements are made at a distance of 4–6 mm from the ball of the joint of the proximal tibia.

The ovariectomy reduces the density of the trabecular bone in the measured area by about 400 mg of $Ca^{2+}/cm^3$ to about 300 mg of $Ca^{2+}/cm^3$. By treatment with a compound of general formula I according to this invention, the degradation of the bone density is prevented or inhibited. The bone density in the proximal tibia was measured.

In considerably smaller amounts, the compounds according to the invention, which produce a 50% bone protection in comparison to the amounts that produce a 50% uterus stimulation, reflect in vivo the higher binding affinity to the estrogen receptor of rat prostates than to the estrogen receptor of rat uteri, relative to the bone mass loss, which can be measured in ovariectomized, untreated female rats 28 days after the ovariectomy unlike in intact animals that are subjected to sham operations.

The vascular action of the estrogens according to the invention is determined in the model of the ApoE-knockout mouse, as described by R. Elhage et al., 1997 (Elhage, R. et al. 1997, Arteriosclerosis, Thrombosis and Vascular Biology 17: 2679–2684).

To detect the action of estrogens in the brain function, the oxytocin receptor mRNA expression is used as a surrogate parameter (Hrabovszky, E. et al. 1998, Endocrinology 1339: 2600–2604). Ovariectomized rats are treated for 7 days with the test substance or vehicle (administration: subcutaneous or oral, six times daily). On day 7 after the first administration, the animals are decapitated, the uterus weight is determined, and the oxytocin receptor mRNA level is studied by means of in situ hybridization in suitable brain sections. The $ED_{50}$ values are determined with respect to stimulation of uterus growth and induction of the oxytocin receptor mRNA.

Another possibility to detect in vivo the dissociated estrogen action of the substances according to the invention consists in that after one-time administration of the substances in rats, effects on the expression of the 5HT2a-receptor and serotonin transporter protein and mRNA levels in ERβ-rich brain areas can be measured. Comparable to the effect on the serotonin receptor and transporter expression, the effect on the LH-secretion is measured. Substances with higher binding to the rat prostates—compared to the rat uterus estrogen receptor—are more powerful with respect to the elevation of the expression of serotonin receptors and transporters, in comparison to their positive effect on the LH-release. The density of serotonin receptors and transporters is determined in the brain sections by means of radioactive ligands, and the corresponding mRNA is determined by means of in situ hybridization. The method is described in the literature: G. Fink & B. E. H. Sumner 1996 Nature 383: 306; B. E. H. Sumner et al. 1999 Molecular Brain Research, in press.

In accordance with the stronger binding to rat prostates—in comparison to the rat uterus-estrogen receptor—substances A, B, C, D and E according to the invention result in an elevated expression of the serotonin receptor and transporter.

Production of the Compounds According to the Invention

For the production of the gonatrienes (=18-nor-estratrienes), two synthesis strategies are known in the literature:

1. Synthesis according to Coombs and Pinhey: M. M. Coombs, C. W. Vose, J. C. S. Chem. Comm. 1974, 602; J. C. Chapman, J. T. Pinhey, Austr. J. Chem. 1974, 2421; as well as A. Kuhl, H. Karels, W. Kreiser, Helv. Chem. Acta 1999, 30;

2. Synthesis according to Zeelen; M. J. van den Heuvel, C. W. van Bokhoven, H. P. de Jongh, F. J. Zeelen, Recl. Trav. Chim. Pays-Bas 107, 1988, 331.

Synthesis According to Zeelen

This synthesis method is suitable for the synthesis of 11β-substituted 18-nor-steroids.

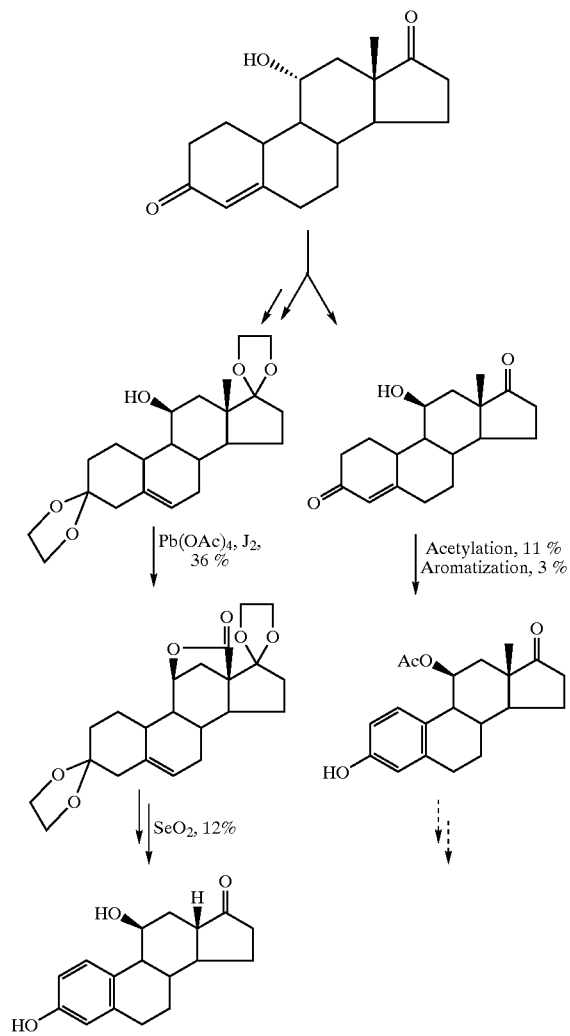

According to this method as well as subsequent other functionalizations at numerous positions of the steroid skeleton, gestagenic 18-nor-3-keto-$\Delta^4$ derivatives with a varied substitution pattern on the steroid can be obtained according to DE 195 35 851 A1. By subsequent aromatization of the 18-nor-3-keto-$\Delta^4$ derivatives, compounds of general formula I according to the invention can be produced. This synthesis route is suitable in particular for the production of those compounds in which the 11-position is substituted. 11-Keto-groups that can be obtained via the 11-hydroxy group or by oxidation from it can be synthesized by functionalization, e.g., by a Wittig reaction, of numerous other substituents according to the methods that are known to one skilled in the art.

This process is illustrated by Examples 10 and 11.

According to these examples, the aromatization is carried out with selenium dioxide.

The aromatization can equally be achieved with the microbiological processes that are known to one skilled in the art.

A type screening yielded that the following microorganisms can perform the reaction:

| | |
|---|---|
| Bacillus lentus | ATCC 13805 |
| Corynebacterium simplex | ATCC 6946 |
| Nocardia corallina | ATCC 14350 |
| Nocardia globerula | ATCC 9356 |

The best results can be achieved with the strain *Bacillus lentus* ATCC 13085. This strain was therefore used for the preparative reactions.

Examples 12 to 14 are used for illustration.

The sequence of the reaction steps for the introduction of functional groups in the steroid skeleton, for example the introduction of a side chain at carbon atom 17 by nucleophilic addition, and the aromatization can also be reversed.

Synthesis According to Coombs and Pinhey

This synthesis route is set forth below in the example of the production of the unsubstituted 18-nor-17β-estradiol.

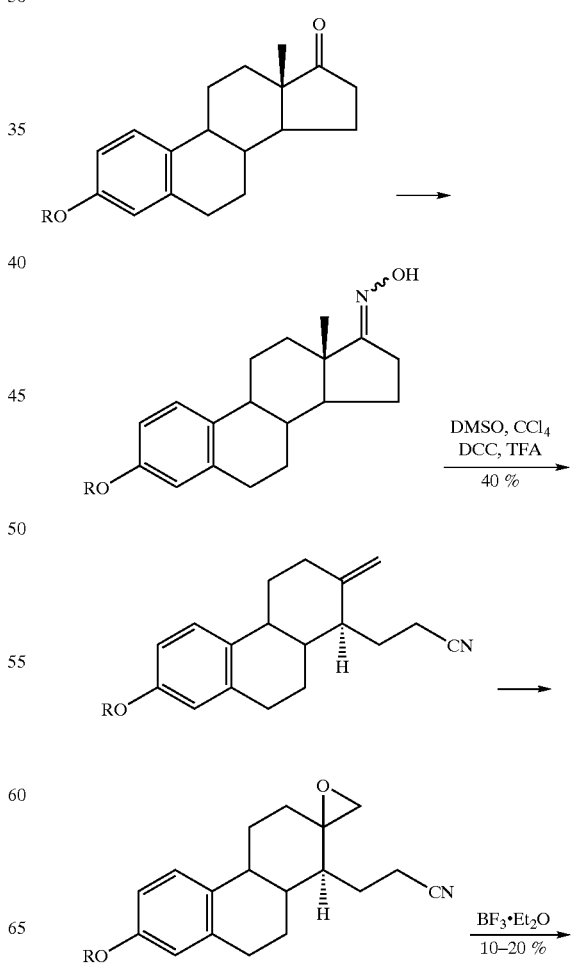

-continued

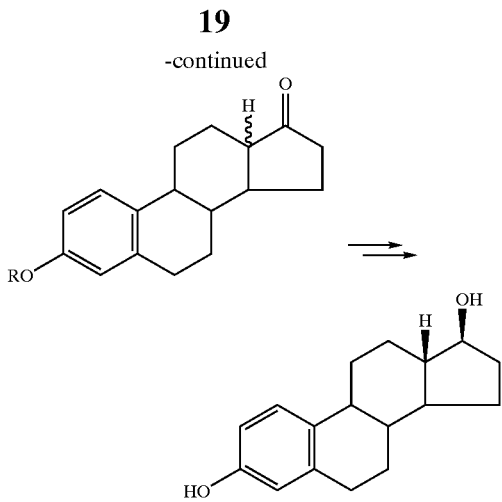

The opening of the D-ring by anomalous Beckmann reaction can be performed with a yield of about 40%; the total yield of the next two steps is about 17% in each case. This synthesis method for the production of the compounds of general formula I according to the invention is illustrated in Examples 1 to 9.

According to general formula I, possible substituents can already be present in the final form or in the form of a precursor already in the starting product, a substituted estrone that already corresponds to the desired end product.

Substituents at carbon atom 7 are introduced according to the process that is known to one skilled in the art and that is commonly used, for example, in the field of antiestrogenic active ingredients by copper-catalyzed 1,6-addition of the substituent or a reactive precursor of it to a 3-keto-$\Delta^{4,6}$ compound, and said substituents are optionally further synthesized (EP 0 138 504 B, WO 98/07740, WO 99/33855).

The introduction of a substituent or reactive precursor at carbon atom 7 is also possible by nucleophilic addition of the substituent or precursor to a 6-vinyl sulfone (DE 42 18 743 A1).

In the last two cases mentioned above, 7α- and 7β-substituted compounds, which can be separated by, for example, chromatographic processes, can be obtained in various portions, independently of the reactants and the selected reaction conditions.

Also according to known processes, 17-substituents are introduced by nucleophilic addition of the desired substituent or a reactive precursor thereof and are optionally further synthesized.

Substituents according to general formula I can also be introduced in the stage of the 18-nor steroids, however. This can be useful or necessary especially in the case of repeated substitution of the desired final compound.

For example, an 11α-hydroxy group can be converted into an 11β-fluorine atom according to the process described by vorbrüggen et al.

Functionalizations at carbon atom 2 are possible, for example, by electrophilic substitution according to prior deprotonation of position 2 of the corresponding 3-(2-tetrahydropyranyl) ether or 3-methyl ether with a lithium base (e.g., methyllithium, butyllithium). Thus, for example, a fluorine atom can be introduced by reaction of the C—H-activated substrate with a fluorinating reagent such as N-fluoromethanesulfonimide (WO 94/24098).

The introduction of variable substituents in rings B, C and D of the gonatriene skeleton can take place in this case according to the same chemical teaching with which the corresponding estratriene derivatives are produced (see, i.a.: Steroide [Steroids], L. F. Fieser, M. Fieser, Verlag Chemie, Weinheim/Bergstr., 1961; Organic Reactions in Steroid Chemistry, J. Fried, J. A. Edwards, Van Nostrand Reinhold Company, New York, Cincinnati, Toronto, London, Melbourne, 1972; Medicinal Chemistry of Steroids, F. J. Zeelen, Elsevier, Amsterdam, Oxford, New York, Tokyo, 1990). This relates to, for example, the introduction of substituents, such as hydroxyl or alkyloxy groups, alkyl, alkenyl or alkinyl groups or halogen, especially fluorine.

The 18-nor-steroid-carboxylic acid esters according to the invention are produced analogously to the esters that are derived from natural steroid active ingredients (see, e.g., Pharmazeutische Wirkstoffe, Synthesen, Patente, Anwendungen [Pharmaceutical Active Ingredients, Syntheses, Patents, Uses]; A. Kleemann, J. Engel', Georg Thieme Verlag Stuttgart 1978, Arzneimittel, Fortschritte [Pharmaceutical Agents, Improvements] 1972 to 1985; A. Kleemann, E. Lindner, J. Engel (Editors), VCH 1987, pp. 773–814).

The 18-nor-steroid sulfamates according to the invention are available in a way that is known in the art from the corresponding hydroxy steroids by esterification with sulfamoyl chlorides in the presence of a base (Z. Chem. 15, 270–272 (1975); Steroids 61, 710–717 (1996)). Subsequent acylation of the sulfamide group results in the 18-nor-steroidal (N-acyl)sulfamates according to the invention for which pharmacokinetic advantages were already demonstrated in the 13-methyl series (cf. DE 195 40 233 A1).

The regioselective esterification of the polyhydroxylated steroids with N-substituted and N-unsubstituted sulfamoyl chlorides is carried out according to partial protection of the hydroxyl groups that are to remain unesterified. Silylethers have proven their value as protective groups with selective reactivity that is suitable for this purpose, since the latter are stable under the conditions of the sulfamate formation, and the sulfamate group remains intact when the silyl ethers are cleaved off again in the regeneration of the residual hydroxyl group still contained in the molecule (Steroids 61, 710–717 (1996)).

The production of the sulfamates according to the invention with one or more additional hydroxyl groups in the molecule is also possible in that a start is made from suitable hydroxy steroid ketones. First, depending on the goal, one or more existing hydroxyl groups are subjected to sulfamoylation. Then, the sulfamate groups optionally can be converted into the (N-acyl)sulfamates in question with a desired acyl chloride in the presence of a base. The oxosulfamates or oxo-(N-acyl)sulfamates that are now present are converted by reduction into the corresponding hydroxysulfamates or hydroxy-(N-acyl)sulfamates (Steroids 61, 710–717 (1996)).

As suitable reducing agents, sodium borohydride and the borane-dimethyl sulfide complex are suitable.

The compounds of general formula I according to the invention are produced as described in the examples. By an analogous procedure using homologous reagents in the reagents that are described in the examples, additional compounds of general formula I can be obtained.

Etherification and/or esterification of free hydroxy groups is carried out according to methods that are common to one skilled in the art.

The compounds according to the invention can be present in carbon atoms 6, 7, 11, 13, 15, 16, and 17 as α,β-stereoisomers. In the production of compounds according to the described processes, the compounds accumulate in most cases as mixtures of the corresponding α,β-isomers. The mixtures can be separated by, for example, chromatographic processes.

The examples below are used for a more detailed explanation of the invention:

EXAMPLES

Example 1

11β-Fluoro-gona-1,3,5(10)-triene-3,17-diol 1.1 11β-Fluoro-1,3,5(10)-estratrien-3-ol-17-one 43.55 g of 11β-fluoro-4-estren-17-ol-3-one (150 mmol, Tetrahedron Letters 1995, 2611) is suspended in 1500 ml of acetonitrile, 50 g of copper(II) bromide is added, and it is stirred at room temperature. After 16 hours, additional copper(II) bromide is added in three portions (25 g, 12 g, 6 g) within 6 hours, and finally stirred for another 6 hours at room temperature. The reaction mixture is cooled in an ice bath, mixed with 500 ml of water and extracted with ethyl acetate. The organic phase is mixed with a little methanol, washed with saturated bicarbonate solution and common salt solution and dried with sodium sulfate. After concentration by evaporation, the substance crystallizes out, yield 30.8 g (71% of theory), flash point 233–234° C.

1.2 11β-Fluoro-3-mesyloxy-estra-1,3,5(10)-trien-17-one 28.84 g of 11β-fluoro-1,3,5(10)-estratrien-3-ol-17-one (100 mmol) is dissolved in 200 ml of pyridine, cooled in an ice bath, 20 ml of methanesulfonic acid chloride is added in drops, and it is stirred for 2 hours at room temperature. Then, it is stirred into 2.5 liters of ice water, and after two hours of stirring, it is filtered off. The solid residue is dissolved in dichloromethane, the solution is shaken out with 1N hydrochloric acid, water and saturated common salt solution and dried with $Na_2SO_4$. After the solvent is drawn off, the residue is 37 g, and after crystallization from methanol, 33.6 g of 11β-fluoro-3-mesyloxy-estra-1,3,5(10)-trien-17-one (91% of theory), flash point, is obtained.

1.3 11β-Fluoro-3-mesyloxy-17-oximinoestra-1,3,5(10)-triene

This substance is suspended in 500 ml of ethanol, mixed with 20 g of hydroxylaminohydrochloride and 40 g of anhydrous sodium acetate, and it is refluxed for 2.5 hours. After cooling, it is diluted with ethyl acetate, washed with water, saturated bicarbonate solution and common salt solution, and the organic phase is dried with sodium sulfate and concentrated by evaporation. The residue is crystallized from ethanol, yield 31.8 g (91% of theory), flash point.

1.4 11β-Fluoro-3-mesyloxy-13,17-seco-estra-1,3,5(10),13 (18)-tetraene-17-nitrile 2.3 g of 11β-fluoro-3-mesyloxy-17-oximidoestra-1,3,5 (10)-triene (6.3 mmol) is dissolved in 10 ml of dimethyl sulfoxide and 10 ml of carbon tetrachloride, 3.9 g of dicyclohexylcarbodiimide is added, and it is cooled in an ice bath. Then, 0.33 ml of trifluoroacetic acid is added in drops, and it is,stirred for 3 hours, whereby the temperature increases to +9° C. The reaction mixture is now added to ice water, shaken out three times with dichloromethane, the organic phase is washed with water, saturated bicarbonate solution and common salt solution, dried with sodium sulfate and concentrated by evaporation. The residue of 4.4 g is chromatographed on silica gel with a hexane-ethyl acetate mixture, yield 0.79 g (36% of theory) as a colorless oil.

1.5 13(18)-Epoxy-11β-fluoro-3-mesyloxy-13,17-seco-estra-1,3,5(10)-triene-17-nitrile 256 mg of seconitrile (0.7 mmol) is dissolved in 10 ml of dichloromethane, 500 mg of m-chloroperbenzoic acid (70%) is added in two portions, and it is stirred for 20 hours at room temperature. The mixture is washed with 10% potassium iodide solution, 1 molar sodium dithionite, saturated bicarbonate solution and common salt solution, dried with sodium sulfate and concentrated by evaporation. The residue (280 mg) is chromatographed on silica gel with hexane and ethyl acetate, yield 131 mg (49% of theory) as a colorless oil (isomer mixture).

1.6 11β-Fluoro-3-mesyloxy-gona-1,3,5(10)-trien-17-one 571 mg of the epoxide above (1.5 mmol) is dissolved in 200 ml of toluene, 1.3 ml of boron trifluoride etherate is added, and it is heated for 16 hours to 110° C. After cooling, the mixture is diluted with ethyl acetate, washed with saturated bicarbonate and common salt solution, dried with sodium sulfate and. concentrated by evaporation. The residue of 577 mg is chromatographed on silica gel with hexane and acetone, yield 90 mg (17% of theory) as a solid foam.

1.7 11β-Fluoro-gona-1,3,5(10)-triene-3,17-diol 200 mg of lithium aluminum hydride is added to the solution of 90 mg of 11β-fluoro-3-mesyloxy-gona-1,3,5 (10)-trien-17-one in 10 ml of anhydrous THF, and it is stirred for 2 hours while being cooled with ice, for 16 hours at room temperature and for 1 hour under reflux. After cooling, it is mixed with saturated common salt solution, extracted with ethyl acetate, the organic phase is dried with sodium sulfate, and the solvent is concentrated by evaporation. The residue is chromatographed on silica gel with hexane and ethyl acetate, 42 mg of 11β-fluoro-gonadiol (59% of theory) is isolated as a solid foam.

Example 2

11β-Methyl-gona-1,3,5(10)-triene-3,17-diol 2.1 11β-Methyl-3-mesyloxy-estra-1,3,5(10)-17-one 28.4 g of 11β-methyl-estra-1,3,5(10)-3-ol-17-one (100 mmol, Gantchev, J. Med. Chem 1994, 4164) is converted into the mesylate as described in Example 1.2, yield 33.5 g (92% of theory) as a solid foam.

2.2 11β-Methyl-3-mesyloxy-17-oximinoestra-1,3,5(10)-triene

The production of the oxime is carried out as described in Example 1.3 with a yield of 89% (34.0 g), flash point.

2.3 11β-Methyl-3-mesyloxy-13,17-seco-estra-1,3,5(10),13 (18)-tetraene-17-nitrile The oxime is converted into the seco compound as described in Example 1.4, and it accumulates as a solid foam in a yield of 9.1 g (28% of theory).

2.4 13(18)-Epoxy-11β-methyl-3-mesyloxy-13,17-seco-estra-1,3,5(10)-triene-17-nitrile The epoxidation is performed as described in Example 1.5 and yields 6.7 g of epoxide (71% of theory) as a colorless oil.

2.5 11β-Methyl-3-mesyloxy-gona-1,3,5(10)-trien-17-one

The gonadiol derivative as described in Example 1.6 is obtained in a yield of 14% of theory (780 mg) by cyclization with boron trifluoride etherate.

2.6 11β-Methyl-gona-1,3,5(10)-triene-3,17-diol

The reduction of the carbonyl group and cleavage of the protective group with lithium alanate into the end product (as in Example 1.7) is accomplished with a yield of 48% (290 mg).

Example 3

11β-Ethyl-gona-1,3,5(10)-triene-3,17-diol

As described in Example 1, the 11β-ethyl-18-nor-estradiol is produced from 11β-ethyl-estra-1,3,5(10)-trien-3-ol-17-one (Pomper, J. Med. Chem. 1990, 3143) in a total yield of 1.3%, flash point.

Example 4

11β-Phenyl-gona-1,3,5(10)-triene-3,17-diol

In the same way, the corresponding 18-nor compound is produced from 11β-phenyl-estra-1,3,5(10)-trien-3-ol-17-one (Tedesco, J. Org. Chem. 1995, 5316), total yield 0.7%, flash point.

Example 5

7α-Fluoro-gona-1,3,5(10)-triene-3,17-diol

5.1 3-Benzyloxy-7β-hydroxy-estra-1,3,5(10)-trien-17-one 12.83 g (75 mmol) of benzylbromide is added to a suspension of 20 g (67.74 mmol) of 3,7β-dihydroxy-estra-1,3,5(10)-trien-17-one, 3.55 g (148.23 mmol) of lithium hydroxide in 700 ml of dry dimethylformamide, and it is stirred under an argon atmosphere for 30 minutes at 100° C. For working-up, the reaction solution is poured into tartaric-acid ice water, the precipitated product is suctioned off and dried in air. The crude product is taken up in dichloromethane, the organic phase is washed with water and dried on sodium sulfate. After the solvent is drawn off in a vacuum, it is chromatographed on silica gel (dichloromethane-ethyl acetate, gradient of up to 3:2), yield 22.81 g (87%).

5.2 3-Benzyloxy-7α-fluoro-estra-1,3,5(10)-trien-17-one 1.50 g (4 mmol) of 7β-alcohol with 1.52 g (10 mmol) of DBU is introduced into 30 ml of dry toluene, cooled to 0° C. while being stirred and in a moisture-free environment (argon atmosphere), and it is mixed drop by drop with 1.51 g (5 mmol) of perfluorobutanesulfonic acid fluoride in 10 ml of toluene. Then, the ice bath is removed, and it is allowed to stir for 5 more hours at room temperature. For working-up, it is diluted with ethyl acetate (150 ml), the organic phase is washed first with dilute hydrochloric acid, then with sodium hydroxide solution and finally with water/brine. It is allowed to dry on sodium sulfate, concentrated by evaporation in a vacuum, and the residue is identified with ethyl acetate. After concentration by evaporation was again performed, the residue is chromatographed on silica gel (toluene-ethyl acetate, gradient of up to 95:5), yield 0.35 g (23%).

5.3 3-Benzyloxy-7α-fluoro-gona-1,3,5-trien-17-one

3-Benzyloxy-7α-fluoro-gona-1,3,5(10)-trien-17-one is obtained from 37.8 g of 3-benzyloxy-7α-fluoro-estra-1,3,5-trien-17-one as described in Examples 1.2 to 1.6 in a yield of 1.03 g (2.8% of theory) as a solid foam.

5.4 7α-Fluoro-18-nor-1,3,5(10)-trien3-ol-17-one 0.30 g (0.79 mmol) of benzylated 7α-fluoro-18-nor-estrone is mixed with a mixture that consists of 3 ml of thioanisole and 2 ml of trifluoroacetic acid, and it is allowed to stand overnight at room temperature under a cover gas and in a moisture-free environment. For working-up, it is stirred into ice/potassium hydroxide solution, extracted with ethyl acetate, the organic phase is washed neutral and dried on sodium sulfate. The crude product is chromatographed on silica gel (toluene-ethyl acetate, gradient of up to 4:1), yield 0.200 g (87%).

5.5 7α-Fluoro-8-nor-estra-1,3,5(10)-triene-3,17β-diol 0.22 g (0.76 mmol) of 7α-fluoro-18-nor-estrone is dissolved in a mixture that consists of 3 ml of dichloromethane and 9 ml of methanol, and it is mixed in portions under a cover gas atmosphere at 0° C. with 0.35 g of sodium borohydride. Then, it is stirred for 30 more minutes at room temperature, diluted with dichloromethane (150 ml) and worked up into tartaric acid. The organic phase is dried on sodium sulfate after washing with water. The crude product is chromatographed on silica gel after the solvent is drawn off (toluene-ethyl acetate, gradient of up to 1:1), yield 0.22 g (quant.) as a solid foam.

Example 6

7α-Methyl-gona-1,3,5(10)-triene-3,17β-diol

As described in Example 1, 7α-methyl-estra-1,3,5(10)-trien-3-ol-17-one (Ali et al., J. Med. Chem. 1993, 264) is converted into the end product in a yield of 1.8%, flash point.

Example 7

7α-Phenyl-gona-1,3,5(10)-triene-3,17β-diol

7.1 7α-Phenyl-estr-4-ene-3,17-dione 5.76 g of magnesium chips (237 mmol) is suspended in 60 ml of anhydrous THF, and a total of 36.1 g of bromobenzene (230 mmol), dissolved in 100 ml of anhydrous THF, is added slowly and then quickly to start the reaction, and it is heated for 1 hour to 80° C. The mixture of 24 g of copper(I) iodide (120 mmol) and 43 g of lithium bromide (480 mmol) in 115 ml of anhydrous THL is heated to about 50° C., then 40 ml of DMPU is added, and it is stirred for 30 minutes. The solution of phenylmagnesium iodide is cooled to −60° C., and it is slowly mixed with the solution of the copper salt. Then, it is kept at −30° C. for 15 minutes, cooled again to −65° C. and mixed with a solution of 12.4 g of estra-4,6-diene-3,17-dione (46 mmol) in 115 ml of anhydrous THF. After the last addition, the mixture is allowed to heat to −5° C. within 45 minutes, it is cooled again to −40° C., and 15 ml of trimethylchlorosilane (115 mmol) is added. During the next 45 minutes, the internal temperature increases to −18° C., it is mixed with 15 ml of glacial acetic acid, the cooling bath is removed, and it is stirred for another hour. Then, it is diluted with ethyl acetate, washed with semisaturated ammonium chloride solution, saturated bicarbonate solution and common salt solution, the organic phase is dried with sodium sulfate, and the solvent is concentrated by evaporation. The residue is chromatographed on silica gel with hexane, methylene chloride and ethyl acetate. The yield of 7α-phenyl-estr-4-ene-3,17-dione is 8.6 g (54% of theory).

7.2 7α-Phenyl-gona-1,3,5(10)-triene-3,17β-diol

The synthesis sequence is performed as described in Examples 1.1 to 1.7. The yield over all stages is 2.3%.

Example 8

7α-Methyl-gona-1,3,5(10)-triene-1,3,17-triol

8.1 7α-Methyl-estra-1,3,5(10)-triene-1,3-diol-17-one

The solution of 38.4 g of diacetoxy-7α-methyl-1,3,5(10)-estra-1,3,5(10)-trien-17-one (100 mmol; Sauer, Chem. Ber. 1982, 459) is dissolved in 300 ml of anhydrous ethanol, 30 ml of 4n-NaOH is added, and it is heated for 30 minutes to 60° C. Then, the solvent is largely distilled off, the residue is taken up in ethyl acetate and washed neutral with water. The organic phase is dried with sodium sulfate and concentrated by evaporation. The residue is chromatographed on silica gel with benzine-ethyl acetate and crystallized from ethyl acetate/diisopropyl ether, yield 24 g (80% of theory), flash point 228–229° C., $[\alpha_{-D}]=+209°$ (0.5% in pyridine).

8.2 7α-Methyl-gona-1,3,5(10)-triene-1,3,17-triol

The synthesis sequence is performed as described in Examples 1.2 to 1.7. The yield over all stages is 4.5%.

Example 9

2-Fluoro-gona-1,3,5(10)-triene-3,17β-diol

9.1 2-Fluoro-3-methoxy-gona-1,3,5(10)-trien-17β-ol

Starting from 30.2 g of 2-fluoro-3-methoxy-estra-1,3,5(10)-trien-17-one (100 mmol, Diorazio, J. C. S. Perkin I 1992, 421), the synthesis of the 18-nor compound is performed as described in Examples 1.3 to 1.7, yield 5.3%.

9.2 2-Fluoro-gona-1,3,5(10)-triene-3,17-diol

The solution of 0.53 g of 2-fluoro-3-methoxy-gona-1,3,5(10)-trien-17β-ol in 50 ml of toluene is mixed with 5 ml of 20% solution of DIBAH in toluene and heated for 2 hours to 80° C. After cooling, water is added drop by drop until the reaction has run its course, then it is dispersed between water and ethyl acetate, the ethyl acetate phase is washed with concentrated common salt solution and dried with sodium sulfate. After evaporation, a residue remains that is chromatographed on silica gel with hexane-ethyl acetate, and the yield is 0.32 g (63% of theory).

Example 10

11β,17α-Dimethylgona-1,3,5(10)-triene-3,17β-diol
10.1  5,6α-Epoxy-3,3-[1,2-ethanediylbis(oxy)]-11-methylene-5α-gonan-17-one 1.4 g (4.45 mmol) of 3,3-[1,2-ethanediylbis(oxy)-11-methylenegon-5-en-17-one (for production see DE 19535851, Example 2c) is dissolved in 20 ml of dichloromethane. It is mixed with 1.5 ml of saturated aqueous sodium bicarbonate solution, then cooled to 0° C., and 490 mg (18.3 mmol) of 2,2,2-trifluoro-1-(3-nitrophenyl)-ethanone as well as 1.9 ml of hydrogen peroxide (30% aqueous solution, 18.6 mmol) are added at this temperature. Then, it is stirred for 100 hours at 25° C. Then, 9 ml of saturated sodium thiosulfate solution is added to the reaction mixture while being cooled slightly. It is extracted with dichloromethane. The organic phase is washed with 5% sodium hydroxide solution as well as saturated sodium chloride solution and dried on sodium sulfate. Column chromatography of the crude product on silica gel with a mixture that consists of hexane/ethyl acetate yields 1 g (68%) of 10.1.

$^1$H-NMR (CDCl$_3$): d=4.97 (1H), 4.69 (1H), 3.85–4.08 (1H), 3.02 (1H), 2.66 (1H) ppm.

10.2  3,3-[1,2-Ethanediylbis(oxy)]-11-methylene-5α-gonane-5,17β-diol

A solution of 1 g (3.03 mmol) of the compound, described under a), in 10 ml of tetrahydrofuran is added to a suspension of 990 mg (26 mmol) of lithium aluminum hydride in 20 ml of tetrahydrofuran at 0° C. It is stirred for one more hour at 0° C. and then 20 ml of saturated ammonium chloride solution is carefully added. The precipitate that forms is filtered off. The filtrate is diluted with ethyl acetate. The organic phase is then washed with saturated sodium chloride solution and dried on sodium sulfate. Column chromatography of the crude product on silica gel with a mixture that consists of hexane/ethyl acetate yields 980 mg (90%) of 10.2.

$^1$H-NMR (CDCl$_3$): δ=4.88 (1H), 4.54 (1H), 3.90–4.06 (4H), 3.84 (1H) ppm.

10.3  3,3-[1,2-Ethanediylbis(oxy)]-11β-methyl-5α-gonane-5,17β-diol

A solution of 980 mg (2.93 mmol) of the compound, described under b), in 80 ml of ethanol is mixed with 90 mg of palladium/carbon (10%). It is then hydrogenated under 1 atmosphere of hydrogen (reaction time about 20 minutes). Then, it is filtered on Celite/silica gel and concentrated by evaporation in a vacuum. The crude product that is obtained (986 mg (100%)) is used without purification in the next step.

$^1$H-NMR (CDCl$_3$): δ=3.89–4.06 (4H), 3.86 (1H), 3.73 (1H), 0.86 (3H) ppm.

10.4 3,3-[1,2-Ethanediylbis(oxy)]-5-hydrox11β-methyl-5α-gonan-17-one 1.76 g (17.6 mmol) of chromium trioxide is added to 5.9 ml of pyridine in 30 ml of dichloromethane at 0° C. It is allowed to stir for 15 more minutes at 0° C., and then a solution of 986 mg (2.93 mmol) of the compound, described under c), in 10 ml of dichloromethane is added. It is then allowed to stir for one more hour at 0° C., and then washed twice with 5% aqueous sodium hydroxide solution and once with saturated aqueous sodium chloride solution. It is dried on sodium sulfate, and the crude product that is obtained is purified by column chromatography on silica gel with a mixture that consists of hexane/ethyl acetate. 830 mg (85%) of 10.4 is obtained.

$^1$H-NMR (CDCl$_3$): δ=3.92–4.05 (4H), 3.89 (1H), 2.38 (1H), 0.85 (3H) ppm.

10.5  11β,17α-Dimethyl-3,3-[1,2-ethanediylbis(oxy)]-5α-gonane-5,17β-diol (A) and 11β,17β-dimethyl-3,3-[1,2-ethanediylbis(oxy)]-5α-gonane-5,17α-diol (B)

A solution of 260 mg (0.78 mmol) of the compound, described under c), in a mixture that consists of 5 ml of tetrahydrofuran and 5 ml of diethyl ether is added at 0° C. to 4.7 ml of a 1.6 molar solution of methyllithium in diethyl ether. It is allowed to stir for one more hour at 0° C., and then the reaction mixture is poured onto saturated aqueous ammonium chloride solution. It is extracted with ethyl acetate, the organic phase is washed with saturated sodium chloride solution and dried on sodium sulfate. The crude product that is obtained is purified by column chromatography on silica gel with a mixture that consists of hexane/ethyl acetate. 166 mg (61%) of compound A and 60 mg (22%) of compound B are obtained.

$^1$H-NMR (CDCl$_3$):

Compound A: δ=3.90–4.02 (3H), 2.08 (1H), 1.12 (3H), 0.85 (3H) ppm.

Compound B: δ=3.90–4.03 (3H), 2.12 (1H), 1.28 (3H), 0.85 (3H) ppm.

10.6 11β,17α-Dimethyl-17β-hydroxy-gon-4-en-3-one 0.4 ml of 4N hydrochloric acid is added to a solution of 166 mg (0.47 mmol) of compound A, described under e), in 10 ml of acetone. It is allowed to stir for one more hour at 25° C., and then the reaction mixture is poured onto saturated aqueous sodium bicarbonate solution. Then, it is extracted with dichloromethane. The organic phase is washed with saturated sodium chloride solution and dried on sodium sulfate. The crude product that is obtained is purified by column chromatography on silica gel with a mixture that consists of hexane/ethyl acetate. 119 mg (87%) of 10.6 is obtained.

$^1$H-NMR (CDCl$_3$): δ=5.83 (1H), 1.13 (3H), 0.97 (3H) ppm.

10.7 11β,17α-Dimethylgona-1,3,5(10)-triene-3,17β-diol

Lithium diisopropylamide (LDA) is produced in 10 ml of tetrahydrofuran at 0° C. from 0.77 ml of a 1.6 molar solution of n-butyllithium in hexane (1.23 mmol) and 0.18 ml (1.28 mmol) of diisopropylamine. Then, it is cooled to −78° C., and a solution of 119 mg (0.41 mmol) of the compound, described under 10.6, in 8 ml of tetrahydrofuran is added. It is stirred for one more hour at −78° C. Then, 0.16 ml (0.42 mmol) of trimethylchlorosilane is added. It is allowed to come to 0° C. and stirred for another 30 minutes. Then, the reaction mixture is poured onto saturated aqueous sodium bicarbonate solution. It is extracted with ethyl acetate, the organic phase is washed with saturated aqueous sodium chloride solution, dried on sodium sulfate and concentrated by evaporation in a vacuum. The crude silyl enol ether that is obtained (148 mg) is dissolved in 6 ml of acetonitrile. 102 mg (0.45 mmol) of palladium(II) acetate is added, and it is allowed to stir for 2.5 more hours at 25° C. Then, the reaction mixture is filtered on Celite, and the filtrate is concentrated by evaporation in a vacuum. The crude product that is obtained is purified by column chromatography on silica gel with a mixture that consists of hexane/ethyl acetate. 61 mg (52%) of the title compound is obtained.

$^1$H-NMR (CDCl$_3$): δ=7.04 (1H), 6.58 (1H), 6.47 (1H), 2.60–2.75 (3H), 2.40 (1H), 1.14 (3H), 0.72 (3H) ppm.

Example 11

11β,17β-Dimethylgona-1,3,5(10)-triene-3,17α-diol
11.1 11β,17β-Dimethyl-17α-hydroxy-gon-4-en-3-one Analogously to Example 10.6, 40 mg (81%) of 11.1 is obtained from 60 mg (0.17 mmol) of compound B, described under 10.5, by reaction with 4N hydrochloric acid in acetone after column chromatography.

$^1$H-NMR (CDCl$_3$): δ=5.83 (1H), 1.29 (3H), 0.98 (3H) ppm.

11.2 11β,17β-Dimethylgona-1,3,5(10)-triene-3,17α-diol

Analogously to Example 10.7, 23 mg (57%) of 11.2 is obtained from 40 mg (0.14 mmol) of the compound that is described under 11.1.

$^1$H-NMR (CDCl$_3$): δ=7.09 (1H), 6.62 (1H), 6.50 (1H), 2.70–2.85 (3H), 2.48 (1H), 1.29 (3H), 0.78 (3H) ppm.

Example 12

11β-Methyl-17α-(1-propinyl)-gona-1,3,5(10)-triene-3,17β-diol

Substrate amount: 6.0 mg of 17β-hydroxy-11β-methyl-17α-(1-propinyl)-gon-4-en-3-one The production of the title compound with the strain *Bacillus lentus* ATCC 13805 is carried out in a 20 ml fermentation flask.

Preculture: 100 ml of sterile medium that consists of 0.5% glucose, 0.5% yeast extract, 0.1% peptone and 0.2% Coorn steep liquor. (pH 7.5) is inoculated with a slant culture of the strain *Bacillus lentus* ATCC 13805, and it is incubated for 24 hours at 28° C. and 165 rpm in a rotary shaker.

Main culture: For biotransformation, 3×20 ml of the preculture is transferred in each case into one sterile 100 ml shaking flask. At the same time, the substrate 17β-hydroxy-11β-methyl-17α-(1-propinyl)-gon-4-en-3-one is dissolved in an organic solvent and added. The concentration in the culture broth is 100 mg/l. As a solvent, preferably ethanol is used, but other water-miscible solvents, such as, e.g., dimethylformamide, can also be used. The incubation is performed at 28° C. and 165 rpm in a rotary shaker. The control of the reaction is carried out with use of methods such as thin-layer chromatography or preferably HPLC. After 28 hours, the reaction is completed. The culture broth of the three shaking flasks is extracted once with 1 volume of methyl isobutyl ketone each, the organic phases are combined and evaporated to the dry state under a vacuum.

Isolation: The isolation and purification of the reaction product 11β-methyl-17α-(1-propinyl)-gona-1,3,5(10)-triene-3,17β-diol are carried out (because of the small amount) via HPLC under the following conditions:

Column: Semi-prep-column of the Phenomenex Company (LUNA 5μ, SILICA (2), 250×10 mm),
Flow agent: Hexane/dioxane 75/25
Flow rate: 5 ml/min
Yield: 42% 11β-Methyl-17α-(1-propinyl)-gona-1,3,5(10)-triene-3,17β-diol

Example 13

11-Methylene-17α-(1-propinyl)-gona-1,3,5(10)-triene-3,17β-diol

Analogously to Example 12, the title compound is obtained in a yield of 90% from 20 mg of 17β-hydroxy-11-methylene-17α-(1-propinyl)-gon-4-en-3-one.

Example 4

17α-(1-Propinyl)-gona-1,3,5(10)-triene-3,17β-diol

Analogously to Example 12, the title compound is obtained with a yield of 40% from 6 mg of 17β-hydroxy-17α-(1-propinyl)-gon-4-en-3-one.

TABLE 1

| Estrogen | Structure | | hERα RBA* | hER β RBA* | ERβ/ ERα | Rat uterus ER (RBA) | Rat prost. ER (RBA) | Prost. ER/uterus ER |
|---|---|---|---|---|---|---|---|---|
| Estradiol | 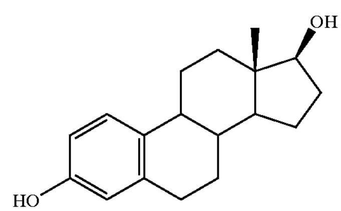 | Chiral | 100 | 100 | 1 | 100 | 100 | 1 |
| Estrone | 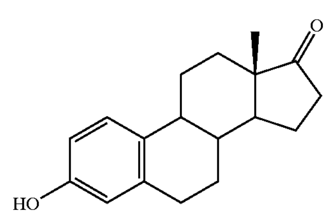 | Chiral | 60 | 37 | 0.6 | 3 | 2 | 0.8 |

TABLE 1-continued

| Estrogen | Structure | hERα RBA* | hERβ RBA* | ERβ/ ERα | Rat uterus ER (RBA) | Rat prost. ER (RBA) | Prost. ER/uterus ER |
|---|---|---|---|---|---|---|---|
| 17α-Estradiol | Chiral | 58 | 11 | 0.2 | 2.4 | 1.3 | 0.5 |
| Estriol | Chiral | 14 | 21 | 1.5 | 4 | 20 | 5 |
| 5-androstenediol | Chiral | 6 | 17 | 3 | 0.1 | 5 | 50 |
| Genisteine | 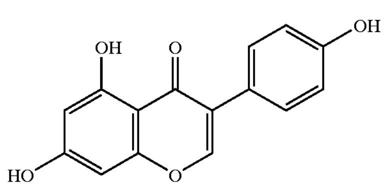 | 5 | 36 | 7 | 0.1 | 10 | 100 |
| Coumestrol | 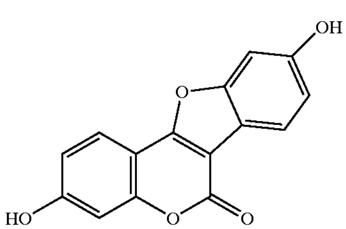 | 94 | 185 | 2 | 1.3 | 24 | 18 |

*Cited from: Kuiper et al. (1996), Endocrinology 138: 863–870.

TABLE 2

| Compound | ER Prostate RBA | ER Uterus RBA |
|---|---|---|
| A | 37 | 3 |
| B | 45 | 26 |
| C | 77 | 4 |
| D | 10 | 0.4 |
| E | 111 | 20 |

What is claimed is:

1. A gona-1,3,5(10)-triene compound of formula I

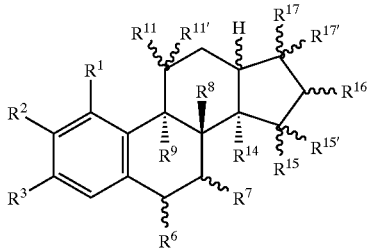

in which
R$^1$ means a halogen atom, or R$^{18}$—O—,
R$^{18}$ means a hydrogen atom or a straight-chain or branched-chain, saturated or unsaturated hydrocarbon radical with up to 6 carbon atoms,
R$^2$ means a hydrogen atom
R$^{19}$ is an R$^{20}$R$^{21}$N group,
R$^{20}$ and R$^{21}$, independently of one another, represent a hydrogen atom, a C$_1$–C$_5$ alkyl radical, a group C(O)R$^{22}$,
R$^{22}$ can contain a straight-chain or branched-chain hydrocarbon radical with up to 12 carbon atoms, which in addition can contain up to three double bonds and/or triple bonds, a C$_3$–C$_7$ cycloalkyl radical, an aryl radical or a combination of these structural features, or, together with the N atom, a polymethylenimino radical with 4 to 6 C atoms or a morpholino radical;
R$^3$ means a group R$^{18}$—O—, R$^{19}$SO$_2$—O— or —O—C(O)R$^{22}$, or an —O-aryl —O-heteroaryl or —O-aralkyl radical;
R$^6$ is hydrogen,
R$^7$ is a hydrogen atom, a halogen atom, a group R$^{18}$—O—, R$^{19}$SO$_2$—O— or —R$^{22}$, a straight-chain or branched-chain, saturated or unsaturated, partially or completely halogenated alkyl group with up to 10 carbon atoms or an optionally substituted aryl, heteroaryl or aralkyl radical,
R$^8$ and R$^9$ are hydrogen,
R$^{11}$ means a hydrogen atom, a halogen atom, a group R$^{18}$—O—, R$^{19}$SO$_2$—O— or —R$^{22}$, a group —X—R$^{18}$, a nitrooxy group, a straight-chain or branched-chain, saturated or unsaturated, partially or completely halogenated hydrocarbon radical with up to 10 carbon atoms or an optionally substituted aryl, heteroaryl or aralkyl radical,
X is an oxygen or sulfur atom,
R$^{11'}$, R$^{14}$, R$^{15}$, R$^{15'}$ and R$^{16}$ each mean a hydrogen atom, and
R$^{17}$ and R$^{17'}$ mean a hydrogen atom and a halogen atom; a hydrogen atom and a group R$^{19}$SO$_2$—O—; hydrogen and a group —O—C(O)R$^{22}$; or hydrogen and —R$^{18}$—O—.

2. A compound according to claim 1, in which
R$^1$ is a hydroxy group.

3. A compound according to claim 1, in which
R$^7$ is a hydrogen atom, a fluorine or chlorine atom, a group R$^{18}$—O—, R$^{19}$SO$_2$—O— or —R$^{22}$, a straight-chain or branched-chain, saturated or unsaturated, partially or completely halogenated alkyl group with up to 10 carbon atoms or an optionally substituted aryl, heteroaryl or aralkyl radical.

4. A compound according to claim 1, in which
X is an sulfur atom,
R$^{11}$ is a hydrogen atom, a halogen atom, a group —R$^{22}$, a group —X—R$^{18}$, a straight-chain or branched-chain, saturated or unsaturated, partially or completely halogenated hydrocarbon radical with up to 10 carbon atoms or an optionally substituted aryl or heteroaryl radical.

5. A compound according to claim 1, in which
X is an sulfur atom,
R$^{18}$ is a saturated, straight-chain or branched-chain C$_1$–C$_6$ alkyl group,
R$^{11}$ is a hydrogen atom, a fluorine or chlorine atom, a saturated, straight-chain or branched-chain C$_1$–C$_6$ alkyl group, a group —X—R$^{18}$, a chloromethyl or chloroethyl group or an optionally substituted aryl or heteroaryl radical.

6. A compound according to claim 1, in which
R$^1$ means a hydroxy group,
R$^7$ means a hydrogen atom, a fluorine or chlorine atom, a group R$^{18}$—O—, R$^{19}$SO$_2$—O— or —R$^{22}$, a straight-chain or branched-chain, saturated or unsaturated, partially or completely halogenated alkyl group with up to 10 carbon atoms or an optionally substituted aryl, heteroaryl or aralkyl radical,
R$^{11}$ means a hydrogen atom, a fluorine or chlorine atom, a saturated, straight-chain or branched-chain C$_1$–C$_6$ alkyl group, a group —X—R$^{18}$, a chloromethyl or chloroethyl group or an optionally substituted aryl or heteroaryl radical,
X is a sulfur atom, and
R$^{18}$ means a saturated, straight-chain or branched-chain C$_1$–C$_6$ alkyl group.

7. A compound according to claim 1, in which
R$^{17}$ and R$^{17'}$ are hydrogen and —R$^{18}$—O—; or hydrogen and a group —O—C(O)R$^{22}$.

8. A compound according to claim 1, in which
R$^3$ means a group R$^{19}$SO$_2$—O— or —O—C(O)R$^{22}$, or an —O-aryl —O-heteroaryl or —O-aralkyl radical.

9. A compound according to claim 1, in which
R$^{17}$ and R$^{17'}$ mean a hydrogen atom and a halogen atom; a hydrogen atom and a group R$^{19}$SO$_2$—O—; or hydrogen and a group —O—C(O)R$^{22}$.

10. A compound which is
11β-Fluoro-gona-1,3,5(10)-triene-3,17-diol
11β-chloro-gona-1,3,5(10)-triene-3,17-diol
11β-methyl-gona-1,3,5(10)-triene-3,17-diol
11β-ethyl-gona-1,3,5(10)-triene-3,17-diol
11β-phenyl-gona-1,3,5(10)-triene-3,17-diol
7α-fluoro-gona-1,3,5(10)-triene-3,17-diol
7α-methyl-gona-1,3,5(10)-triene-3,17β-diol
7α-phenyl-gona-1,3,5(10)-triene-3,17β-diol
7α-methyl-gona-1,3,5(10)-triene-3,17-diol
7β-fluoro-gona-1,3,5(10)-triene-3,17-diol 7β-methyl-gona-1,3,5(10)-triene-3,17β-diol
7βphenyl-gona-1,3,5(10)-triene-3,17β-diol
7β-methyl-gona-1,3,5(10)-triene-3,17-diol
11β-fluoro-gona-1,3,5(10)-triene-1,3,17-triol
11β-chloro-gona-1,3,5(10)-triene-1,3,17-triol
11β-methyl-gona-1,3,5(10)-triene-1,3,17-triol
11β-ethyl-gona-1,3,5(10)-triene-1,3,17-triol
11β-phenyl-gona-1,3,5(10)-triene-1,3,17-triol
7α-fluoro-gona-1,3,5(10)-triene-1,3,17-triol
7α-methyl-gona-1,3,5(10)-triene-1,3,17-triol
7α-phenyl-gona-1,3,5(10)-triene-1,3,17-triol
7α-methyl-gona-1,3,5(10)-triene-1,3,17-triol
7β-fluoro-gona-1,3,5(10)-triene-1,3,17-triol
7β-methyl-gona-1,3,5(10)-triene-1,3,17-triol
7β-phenyl-gona-1,3,5(10)-triene-1,3,17-triol
7β-methyl-gona-1,3,5(10)-triene-1,3,17-triol or
13α-H-18-nor-estradiol.

11. A pharmaceutical composition comprising a compound according to claim 1 and a pharmaceutically compatible vehicle.

12. A method for treating an estrogen-deficiency-induced disease or condition in a woman or man, comprising administering to the woman or man a compound according to claim 1.

13. A method for treating an estrogen-deficiency-induced disease or condition in a woman or man, comprising administering to the woman or man a compound according to claim 10.

14. A method according to claim 12, wherein the estrogen-deficiency-induced disease or condition is a perimenopausal and postmenopausal symptom.

15. A method according to claim 12, wherein the estrogen-deficiency-induced disease or condition is a peri- and post-male-menopausal symptom.

16. A method according to claim 14, wherein the estrogen-deficiency-induced disease or condition is hot flashes, sleep disturbances, irritability, mood swings, incontinence, vaginal atrophy or a hormone-deficiency-induced emotional disease.

17. A method according to claim 16, wherein the disease is in the urogenital tract.

18. A method according to claim 12, wherein the estrogen-deficiency-induced disease or condition is a disease of stomach or intestine.

19. A method according to claim 18, wherein the estrogen-deficiency-induced disease or condition is an ulcer or a hemorrhagic diatheses in the gastrointestinal tract.

20. A method according to claim 19, wherein the estrogen-deficiency-induced disease or condition is neoplasia.

21. A method according to claim 12, wherein the estrogen-deficiency-induced disease or condition is male infertility, which is treated in-vitro.

22. A method according to claim 12, wherein the estrogen-deficiency-induced disease or condition is male infertility, which is treated in-vivo.

23. A method according to claim 12, wherein the estrogen-deficiency-induced disease or condition is female infertility, which is treated in-vitro.

24. A method according to claim 12, wherein the estrogen-deficiency-induced disease or condition is female infertility, which is treated in-vivo.

25. A method according to claim 12, wherein the estrogen-deficiency-induced disease or condition is a disease treated with hormone replacement therapy (HRT).

26. A method according to claim 12, wherein the estrogen-deficiency-induced disease or condition is hormone-deficiency-induced bone mass loss.

27. A method according to claim 26, wherein the estrogen-deficiency-induced disease or condition is osteoporosis.

28. A method according to claim 12, wherein the estrogen-deficiency-induced disease or condition is a cardiovascular disease.

29. A method according to claim 12, wherein the estrogen-deficiency-induced disease or condition is a vascular disease.

30. A method according to claim 29, wherein the estrogen-deficiency-induced disease or condition is arteriosclerosis.

31. A method according to claim 29, wherein the estrogen-deficiency-induced disease or condition is neointimal hyperplasia.

32. A method according to claim 12, wherein the estrogen-deficiency-induced disease or condition is a hormone-deficiency-induced neurodegenerative disease.

33. A method according to claim 12, wherein the estrogen-deficiency-induced disease or condition is a hormone-deficiency-induced impairment of memory and learning capacity, wherein Alzheimer's disease is optionally also treated.

34. A method according to claim 12, wherein the estrogen-deficiency-induced disease or condition is an inflammatory disease or a disease of the immune system.

35. A method according to claim 12, wherein the estrogen-deficiency-induced disease or condition is benign prostate hyperplasia (BPH).

* * * * *

UNITED STATES PATENT AND TRADEMARK OFFICE
CERTIFICATE OF CORRECTION

PATENT NO.        : 6,958,327 B1                                               Page 1 of 1
APPLICATION NO. : 10/111933
DATED             : October 25, 2005
INVENTOR(S)       : Alexander Hillisch It is certified that error appears in the above-identified patent and that said Letters Patent is hereby corrected as shown below:

Column 31, line 30 reads "$R^2$ means a hydrogen atom" should read -- $R^2$ means a hydrogen atom, --
Column 31, line 43 reads "(O)$R^{22}$, or an –O-aryl –O-heteroaryl" should read
-- (O)$R^{22}$, or an –O-aryl, –O-heteroaryl --
Column 32, line 50 reads "–O-aryl –O-heteroaryl" should read
-- –O-aryl, –O-heteroaryl --
Column 33, line 2 reads "7ßphenyl-gona" should read -- 7ß-phenyl-gona --

Signed and Sealed this

First Day of May, 2007

JON W. DUDAS
*Director of the United States Patent and Trademark Office*